US009915750B2

United States Patent
Hurlimann et al.

(10) Patent No.: US 9,915,750 B2
(45) Date of Patent: Mar. 13, 2018

(54) METHODS AND APPARATUSES TO REMOVE A NET DETECTED RESIDUAL MAGNETIZATION IN A NUCLEAR MAGNETIC RESONANCE (NMR) OPERATION

(71) Applicant: Schlumberger Technology Corporation, Sugar Land, TX (US)

(72) Inventors: Martin D. Hurlimann, Newton, MA (US); Yi-Qiao Song, Newton Center, MA (US); Jeffrey L. Paulsen, Brookline, MA (US); Shin Utsuzawa, Missouri City, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 517 days.

(21) Appl. No.: 14/516,404

(22) Filed: Oct. 16, 2014

(65) Prior Publication Data
US 2016/0109612 A1 Apr. 21, 2016

(51) Int. Cl.
| | |
|---|---|
| *G01V 3/00* | (2006.01) |
| *G01V 3/32* | (2006.01) |
| *G01V 3/38* | (2006.01) |
| *G01N 24/08* | (2006.01) |
| *G01R 33/561* | (2006.01) |
| *G01R 33/565* | (2006.01) |

(52) U.S. Cl.
CPC ............ *G01V 3/32* (2013.01); *G01N 24/081* (2013.01); *G01V 3/38* (2013.01); *G01R 33/5617* (2013.01); *G01R 33/5659* (2013.01); *G01R 33/56563* (2013.01)

(58) Field of Classification Search
CPC .............. G01R 33/543; G01R 33/5659; G01R 33/3415; G01R 33/36; A61B 5/055
USPC ........................................................ 324/309
See application file for complete search history.

(56) References Cited

U.S. PATENT DOCUMENTS

| | | | | |
|---|---|---|---|---|
| 5,055,790 A | * | 10/1991 | Siuciak | G01R 33/565 324/309 |
| 6,051,973 A | | 4/2000 | Prammer | |
| 6,121,774 A | | 9/2000 | Sun et al. | |

(Continued)

OTHER PUBLICATIONS

Translation of Palmer (JP 03066359 A) listed in the IDS, publication date: Mar. 22, 1991.*

(Continued)

*Primary Examiner* — Walter L Lindsay, Jr.
*Assistant Examiner* — Frederick Wenderoth

(57) ABSTRACT

In one aspect, a nuclear magnetic resonance (NMR) system includes a transmitter to output a main refocusing pulse sequence and at least one subsequent refocusing pulse sequence into a zone of interest, a randomizing pulse module to output a randomizing pulse into the zone of interest to remove a net detected residual magnetization, and a receiver to output an NMR data set from the zone of interest. In another aspect, a method of generating a nuclear magnetic resonance (NMR) data set includes outputting a main refocusing pulse sequence and at least one subsequent refocusing pulse sequence into a zone of interest, outputting a randomizing pulse from a randomizing pulse module into the zone of interest to remove a net detected residual magnetization, and sensing the NMR data set from the zone of interest.

23 Claims, 11 Drawing Sheets

(56) References Cited

U.S. PATENT DOCUMENTS

| | | | |
|---|---|---|---|
| 6,140,817 A | 10/2000 | Flaum et al. | |
| 6,147,489 A | 11/2000 | Freedman et al. | |
| 6,242,913 B1 | 6/2001 | Prammer | |
| 6,472,870 B1* | 10/2002 | Bendall | G01R 33/4608 |
| | | | 324/307 |
| 6,483,305 B1* | 11/2002 | Miyamoto | G01R 33/56518 |
| | | | 324/307 |
| 6,566,874 B1 | 5/2003 | Speier et al. | |
| 6,717,404 B2 | 4/2004 | Prammer | |
| 2003/0107374 A1* | 6/2003 | Chen | G01N 24/081 |
| | | | 324/303 |
| 2004/0008027 A1 | 1/2004 | Prammer | |
| 2004/0032258 A1 | 2/2004 | Blumich | |
| 2005/0275401 A1 | 12/2005 | Blanz et al. | |
| 2013/0181707 A1* | 7/2013 | Blanz | G01V 3/32 |
| | | | 324/303 |

OTHER PUBLICATIONS

International Search Report issued in related PCT application PCT/US2015/055714 dated Jan. 28, 2016, 4 pages.

Freed, et al., "The equivalence between off-resonance and on-resonance pulse sequences and its application to steady-state free precession with diffusion in inhomogeneous field", Journal of Magnetic Resonance, vol. 162, No. 2, Jun. 2003, pp. 328-335.

Hurlimann, "Spin dynamics of Carr-Purcell-Meiboom-Gill-like sequences in grossly inhomogeneous B(0) and B(1) fields and application to NMR well logging", Journal of Magnetic Resonance, 143, No. 1, Mar. 2000, pp. 120-135.

\* cited by examiner

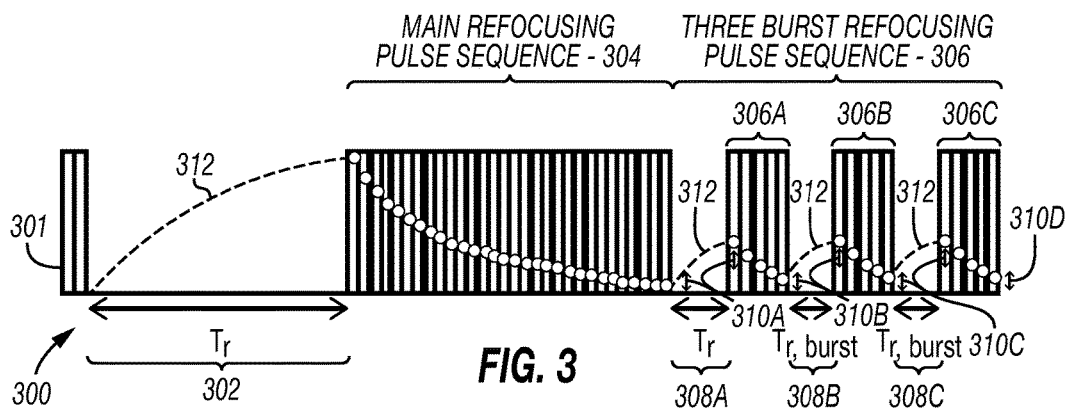
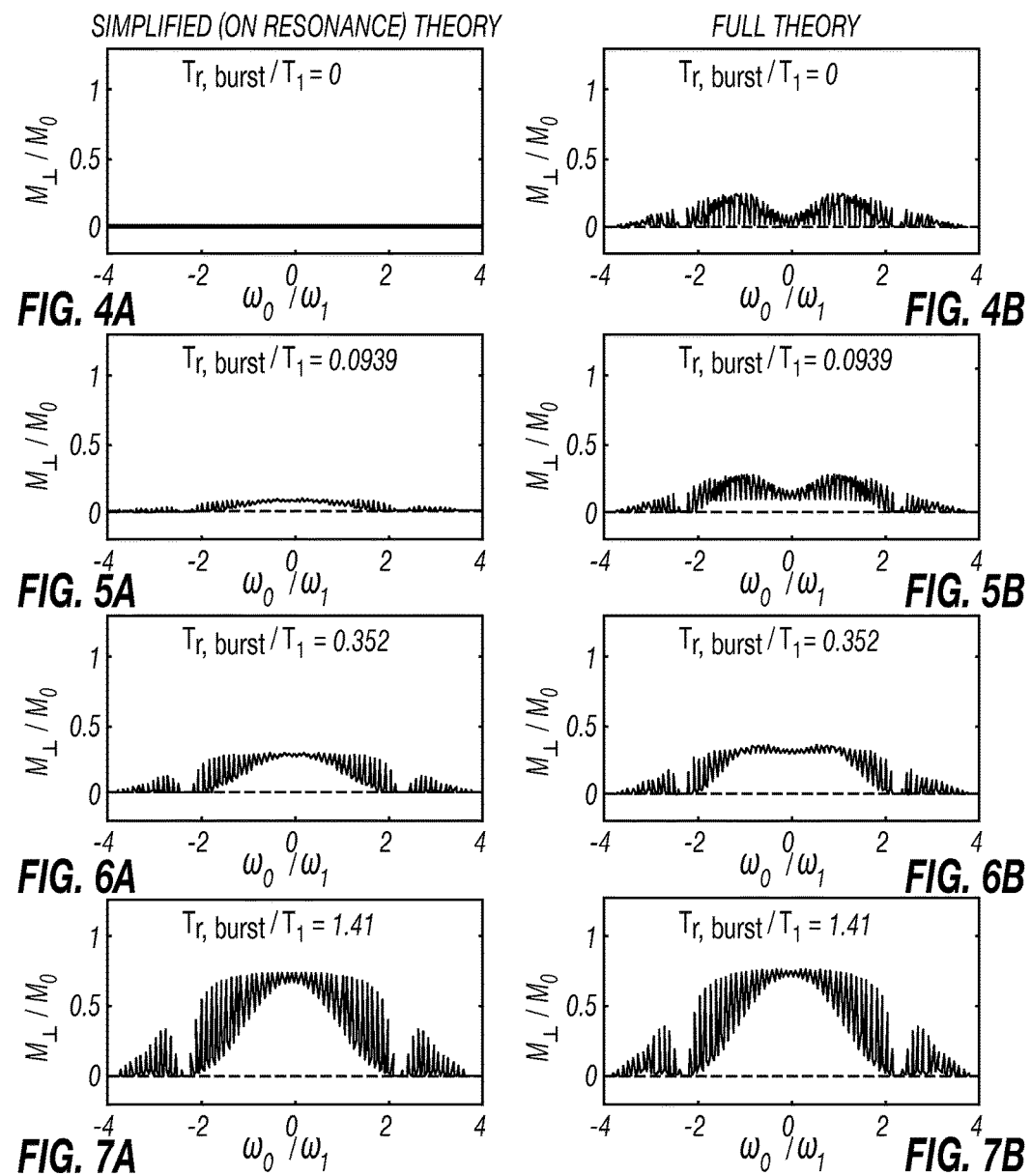

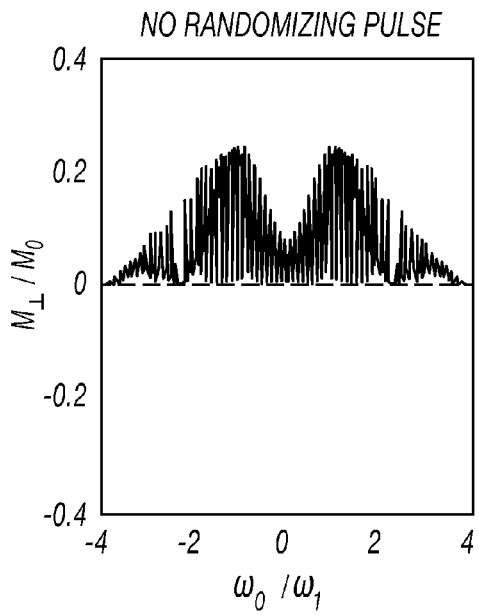
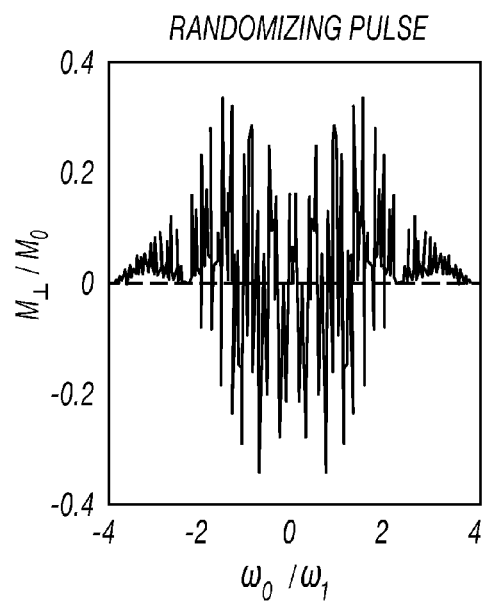
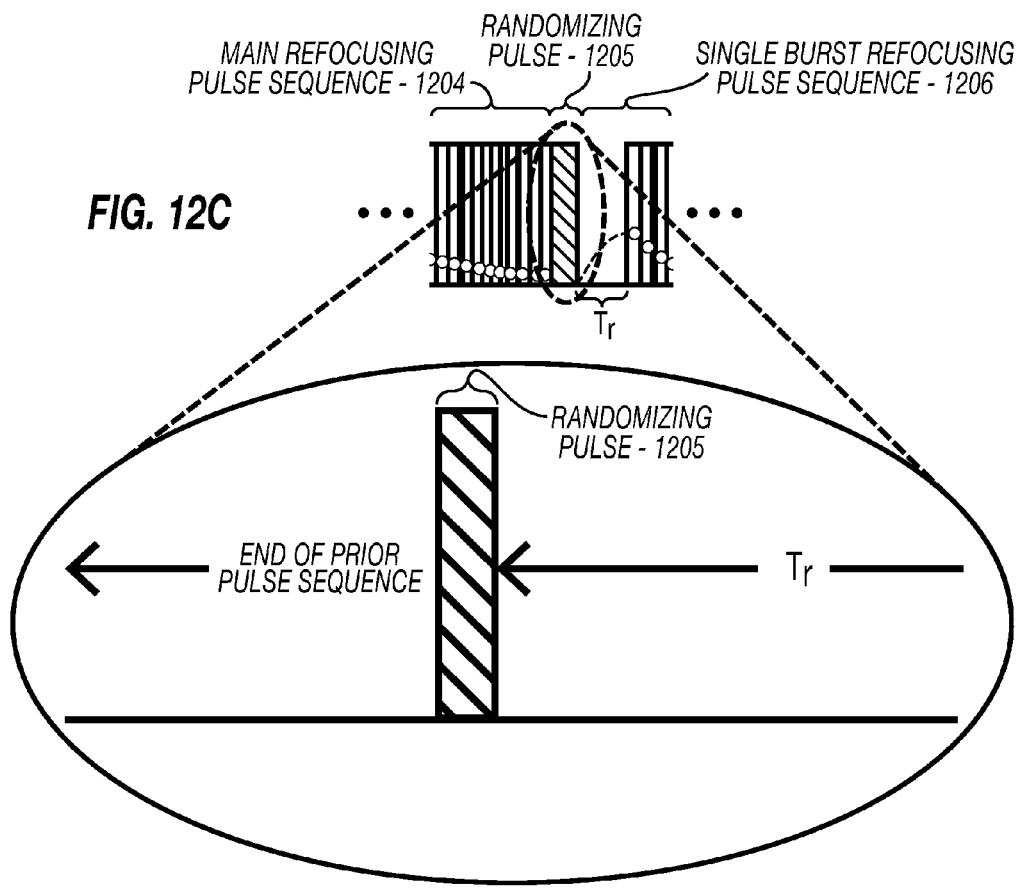

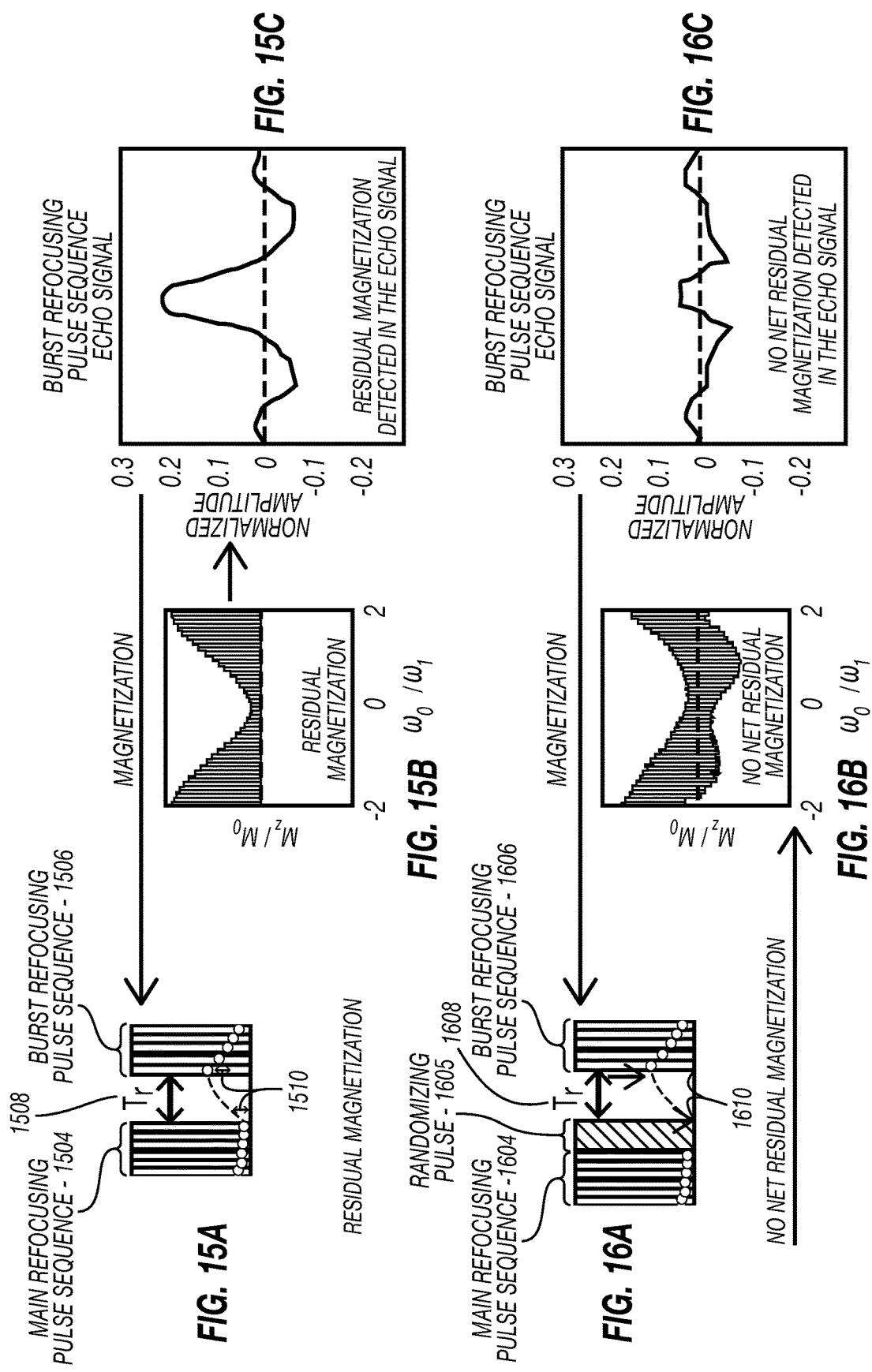

METHODS AND APPARATUSES TO REMOVE A NET DETECTED RESIDUAL MAGNETIZATION IN A NUCLEAR MAGNETIC RESONANCE (NMR) OPERATION

BACKGROUND

1. Technical Field

The present disclosure relates generally to nuclear magnetic resonance (NMR) and, more specifically, to techniques for generating or processing of NMR echo data.

2. Background Information

This section is intended to introduce the reader to various aspects of art that may be related to various aspects of the subject matter described and/or claimed below. This discussion is believed to be helpful in providing the reader with background information to facilitate a better understanding of the various aspects of the present disclosure. Accordingly, it should be understood that these statements are to be read in this light, not as admissions of prior art.

Logging tools may be used in wellbores to make, for example, formation evaluation measurements to infer properties of the formations surrounding the borehole and/or the fluids in the formations. Common logging tools include electromagnetic tools, nuclear tools, acoustic tools, and nuclear magnetic resonance (NMR) tools, though various other types of tools for evaluating formation properties are also available.

Early logging tools were run into a wellbore on a wireline cable after the wellbore had been drilled. Modern versions of such wireline tools are still used. However, as the demand for (e.g., real-time) information while drilling a borehole continued to increase, measurement-while-drilling (MWD) tools and logging-while-drilling (LWD) tools have since been developed. MWD tools typically provide drilling parameter information such as weight on the bit, torque, temperature, pressure, direction, and inclination. LWD tools typically provide formation evaluation measurements such as resistivity, porosity, NMR distributions, and so forth. MWD and LWD tools may have characteristics common to wireline tools (e.g., transmitting and receiving antennas, sensors, etc.), but MWD and LWD tools may be designed and constructed to endure and operate in the environment of drilling.

NMR tools used in well logging generally measure, among other things, relaxation times, such as longitudinal relaxation times ($T_1$) or transverse relaxation times ($T_2$), of formation fluids, which may range from a fraction of a millisecond to several seconds. NMR data may be used to determine properties of a zone of interest, e.g., the substance thereof.

SUMMARY

A summary of certain aspects disclosed herein is set forth below. It should be understood that these aspects are presented merely to provide the reader with a brief summary of certain aspects and that these aspects are not intended to limit the scope of this disclosure. Indeed, this disclosure may encompass a variety of aspects that may not be set forth in this section.

In accordance with one aspect, a nuclear magnetic resonance (NMR) system includes a transmitter to output a main refocusing pulse sequence and a subsequent (e.g., burst) refocusing pulse sequence into a zone of interest, a randomizing pulse module to output a randomizing pulse into the zone of interest to remove a net detected residual magnetization, and a receiver to output an NMR data set from the zone of interest.

In accordance with another aspect, a method of generating a nuclear magnetic resonance (NMR) data set includes outputting a main refocusing pulse sequence and a subsequent (e.g., burst) refocusing pulse sequence into a zone of interest, outputting a randomizing pulse from a randomizing pulse module into the zone of interest to remove a net detected residual magnetization, and sensing the NMR data set from the zone of interest.

In accordance with yet another aspect, an apparatus includes a processor, and a data storage device that stores instructions that, when executed by the processor, causes the processor to perform the following: outputting a main refocusing pulse sequence and a subsequent (e.g., burst) refocusing pulse sequence into a zone of interest, outputting a (e.g., set of) randomizing pulse(s) from a randomizing pulse module into the zone of interest to remove a net detected residual magnetization, and sensing a nuclear magnetic resonance (NMR) data set from the zone of interest.

In accordance with another aspect, an NMR randomizing pulse module includes means to output a randomizing pulse into a zone of interest, e.g., means to remove a net detected residual magnetization from the zone of interest. In accordance with yet another aspect, a method for generating an NMR data set is as described herein. In accordance with another aspect, a system to generate an NMR data set is as described herein. A system and/or method to determine formation porosity may include an NMR randomizing pulse module as described herein. In certain aspects, a burst pulse sequence may be a CPMG pulse sequence.

Again, the brief summary presented above is intended to familiarize the reader with certain aspects and contexts of aspects of the present disclosure without limitation to the claimed subject matter.

BRIEF DESCRIPTION OF DRAWINGS

The present disclosure is illustrated by the following detailed description when read with the accompanying figures. It is emphasized that, in accordance with standard practice in the industry, various features are not necessarily drawn to scale. In fact, the dimensions of various features may be arbitrarily increased or recued for clarity of the discussion.

FIG. 3 is a graph of an NMR pulse sequence without a randomizing pulse according to one aspect of the disclosure.

FIG. 4A is a graph of the simplified (on resonance saturation) theory spectra of the transverse magnetization of a zone of interest from a pulse sequence at a first duration of recovery time ($T_{r,burst}$) preceding it according to one aspect of the disclosure.

FIG. 4B is a graph of the full theory spectra of the transverse magnetization of a zone of interest from a pulse sequence at a first duration of recovery time ($T_{r,burst}$) preceding it according to one aspect of the disclosure.

FIG. 5A is a graph of the simplified (on resonance saturation) theory spectra of the transverse magnetization of a zone of interest from a pulse sequence at a second duration of recovery time ($T_{r,burst}$) preceding it according to one aspect of the disclosure.

FIG. 5B is a graph of the full theory spectra of the transverse magnetization of a zone of interest from a pulse sequence at a second duration of recovery time ($T_{r,burst}$) preceding it according to one aspect of the disclosure.

FIG. 6A is a graph of the simplified (on resonance saturation) theory spectra of the transverse magnetization of a zone of interest from a pulse sequence at a third duration of recovery time ($T_{r,burst}$) preceding it according to one aspect of the disclosure.

FIG. 6B is a graph of the full theory spectra of the transverse magnetization of a zone of interest from a pulse sequence at a third duration of recovery time ($T_{r,burst}$) preceding it according to one aspect of the disclosure.

FIG. 7A is a graph of the simplified (on resonance saturation) theory spectra of the transverse magnetization of a zone of interest from a pulse sequence at a fourth duration of recovery time ($T_{r,burst}$) preceding it according to one aspect of the disclosure.

FIG. 7B is a graph of the full theory spectra of the transverse magnetization of a zone of interest from a pulse sequence at a fourth duration of recovery time ($T_{r,burst}$) preceding it according to one aspect of the disclosure.

FIG. 12A is a graph of the full theory spectra incorporating remnant magnetization effects of the transverse magnetization of a zone of interest from a pulse sequence without a randomizing pulse according to one aspect of the disclosure.

FIG. 12B is a graph of the full theory spectra incorporating remnant magnetization effects of the transverse magnetization of a zone of interest from a pulse sequence including a randomizing pulse according to one aspect of the disclosure.

FIG. 12C is a graph of the implementation of a single randomizing pulse according to one aspect of the disclosure.

FIG. 15A is graph of an NMR pulse sequence without a randomizing pulse according to one aspect of the disclosure.

FIG. 15B is a graph of the full theory spectra incorporating remnant magnetization effects of the transverse magnetization of a zone of interest from a burst refocusing pulse sequence of a pulse sequence without a randomizing pulse according to one aspect of the disclosure.

FIG. 15C is a graph of the echo signal of a burst refocusing pulse sequence of a pulse sequence without a randomizing pulse according to one aspect of the disclosure FIG. 16A is graph of an NMR pulse sequence including a randomizing pulse according to one aspect of the disclosure.

FIG. 16B is a graph of the full theory spectra incorporating remnant of the transverse magnetization of a zone of interest from a burst refocusing pulse sequence of a pulse sequence including a randomizing pulse according to one aspect of the disclosure.

FIG. 16C is a graph of the echo signal of a burst refocusing pulse sequence of a pulse sequence including a randomizing pulse according to one aspect of the disclosure

DETAILED DESCRIPTION

One or more specific aspects of the present disclosure are described below. These aspects are merely examples of the presently disclosed techniques. Additionally, in an effort to provide a concise description of these aspects, all features of an actual implementation may not be described in the specification. It should be appreciated that in the development of any such implementation, as in any engineering or design project, numerous implementation specific decisions are made to achieve the developers' specific goals, such as compliance with system-related and business-related constraints, which may vary from one implementation to another. Moreover, it should be appreciated that such development efforts might be complex and time consuming, but would nevertheless be a routine undertaking of design, fabrication, and manufacture for those of ordinary skill having the benefit of this disclosure.

When introducing elements of various aspects of the present disclosure, the articles "a," "an," and "the" are intended to mean that there are one or more of the elements. The aspects discussed below are intended to be examples that are illustrative in nature and should not be construed to indicate that the specific aspects described herein are necessarily preferential in nature. Additionally, it should be understood that references to "one aspect" or "an aspect" within the present disclosure are not to be interpreted as excluding the existence of additional aspects that also incorporate the recited features.

Figure 1:
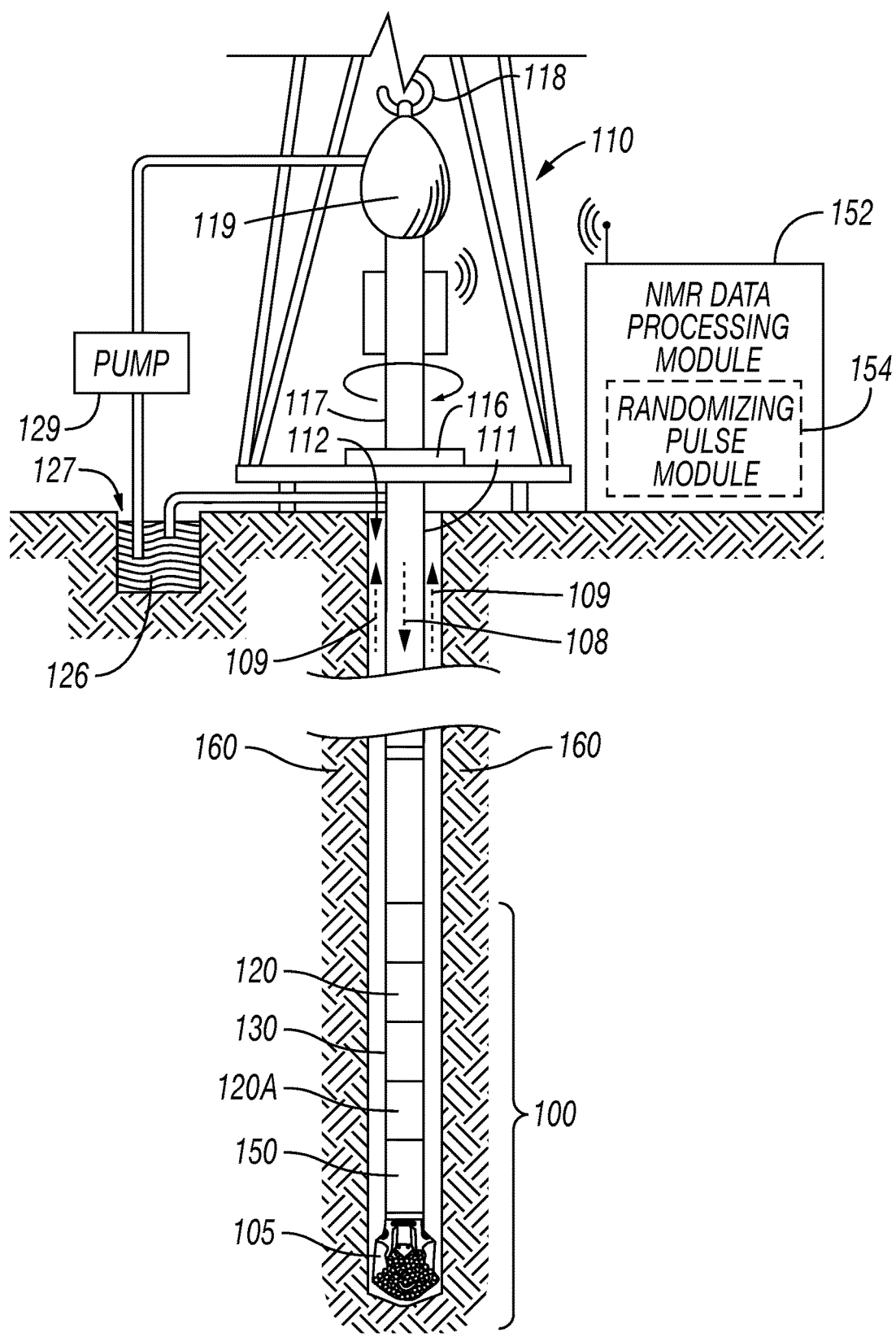
FIG. 1 is a schematic diagram of a well site system that may be used for implementation of an example aspect.

FIG. 1 represents a simplified view of a well site system in which various aspects of this disclosure may be employed. The well site system depicted in FIG. 1 may be deployed in either onshore or offshore applications. In this depicted system, a borehole 111 is formed in a subsurface formation 160 by rotary drilling in a manner that is well known to those skilled in the art. Some aspects may also use directional drilling.

Depicted drill string 112 is suspended within the borehole 111 and has a bottom hole assembly (BHA) 100 which includes a drill bit 105 at its lower end. The surface system includes a platform and derrick assembly 110 positioned over the borehole 111, with the assembly 110 including a rotary table 116, kelly 117, hook 118, and rotary swivel 119 (which in certain aspects may be part of a topdrive drilling motor). In a drilling operation, the drill string 112 may be rotated, e.g. by the rotary table 116 or a topdrive motor. Depicted drill string 112 is suspended from a hook 118, attached to a traveling block (not shown), through the rotary swivel 119 which permits rotation of the drill string 112 relative to the formation 160.

Drilling fluid (e.g., mud) 26 may be stored in a pit 127 formed at the well site. Depicted pump 129 pumps the drilling fluid 126 into the bore of the drill string 112, which causes the drilling fluid 126 to flow downwardly through the drill string 112, as indicated by the directional arrow 108 in FIG. 1. The drilling fluid may exit the drill string 112 via ports in the drill bit 105, and then circulate upwardly through the annulus formed between the outside of the drill string 112 and the inner wall of the borehole 111, as indicated by the directional arrows 109. In this known manner, the drilling fluid may lubricate the drill bit 105 and carry formation cuttings up to the surface as it is returned to the pit 127 for recirculation. In certain aspects, a downhole mud motor 150 may be utilized to rotate the drill bit 105.

Depicted drill string 112 includes a BHA 100 having one measurement while drilling (MWD) module 130 and multiple logging while drilling (LWD) modules 120 (with reference character 120A depicting a second LWD module 120). A single MWD module, a single LWD module, or any combination thereof may be utilized. As used herein, the term "module" as applied to MWD and LWD devices generally refers to either a single tool or a suite of multiple tools contained in a single modular device. Additionally, the depicted BHA 100 includes a rotary steerable system (RSS) including a mud motor 150 to rotate a drill bit 105.

LWD module(s) may be housed in a drill collar and may include one or more types of logging tools. For example, a LWD module may include capabilities for measuring, processing, and storing information, as well as for communicating with the surface equipment. By way of example, the LWD module 120 may include a nuclear magnetic resonance (NMR) logging tool, and may include capabilities for measuring, processing, and/or storing information and/or for communicating (e.g., wirelessly or via mud pulse) with surface equipment. An NMR data processing module 152 may include a nuclear magnetic resonance (NMR) logging tool, and may include capabilities for measuring, processing, and/or storing information and/or for communicating (e.g., wirelessly or via mud pulse) with the downhole equipment. Although the NMR data processing module 152 is depicted at the surface of the formation 160, portions of or the entire NMR data processing module may be disposed in the borehole 111, e.g., with the drill string 112.

Depicted MWD module 130 is also housed in a drill collar, and may contain one or more devices for measuring characteristics of the drill string and drill bit. A MWD module 130 may include one or more of the following types of measuring devices: a weight-on bit measuring device, a torque measuring device, a vibration measuring device, a shock measuring device, a stick/slip measuring device, a direction measuring device, and an inclination measuring device (the latter two sometimes being referred to collectively as a D&I package). The BHA 100 may further include an apparatus (not shown) for generating (e.g., electrical) power for the downhole system. For example, power generated by the MWD tool 130 may be used to power the MWD tool 130 and/or the LWD tool(s) 120. In some aspects, this apparatus may include a mud turbine generator powered by the flow of the drilling fluid 126. It is understood, however, that other power systems (e.g., a battery) may be employed.

The operation of the assembly 110 of FIG. 1 may be controlled using a control system, e.g., located at the surface. A control system may include one or more processor-based computing systems. A processor may include a microprocessor, programmable logic devices (PLDs), field-gate programmable arrays (FPGAs), application specific integrated circuits (ASICs), system-on a-chip processors (SoCs), or any other suitable integrated circuit capable of executing encoded instructions stored on data storage device(s), for example, on tangible computer-readable media (e.g., read memory, random access memory, a hard drive, optical disk, flash memory, etc.). Such instructions may correspond to, for instance, workflows and the like for carrying out a drilling operation, a logging operation, algorithms and routines for processing data received at the surface from the BHA 100 (e.g., as part of an inversion to determine (e.g., obtain) one or more desired formation parameters), and so forth.

An NMR system (e.g., assembly 110 in FIG. 1) may include an NMR data processing module 152, e.g., including one or more processor-based computing systems. A randomizing pulse module 154 may be included as part of an NMR data processing module (e.g., as shown in FIG. 1) or as a separate component (e.g., without an NMR data processing module). An NMR data processing module may be hardware, software, firmware, or any combination thereof. For example, an NMR data processing module may include software, such as stored in memory 1802 in FIG. 18, to generate an NMR data set (e.g., filtered echo data such as, but not limited to, amplitude and/or phase of echo(s) signals). A randomizing pulse module may be hardware, software, firmware, or any combination thereof. For example, a randomizing pulse module of an NMR system may include software, such as stored in randomizing pulse module 1804 in FIG. 18, to remove a net detected residual (e.g., remnant) magnetization from a zone of interest.

Before discussing the techniques set forth in this disclosure, some background with respect to the operation of NMR logging tools is first provided. NMR well logging tools are typically used to determine the properties of nuclear spins in the formation, such as the longitudinal (or spin-lattice) relaxation time (generally referred to as $T_1$), transverse (or spin-spin) relaxation time (generally referred to as $T_2$), and the diffusion coefficient (D) as well as to determine the porosity of the formation from the NMR echo signal, for example, the echo signal amplitude(s). Knowledge of these NMR properties may aid the determination of basic formation properties such as permeability and porosity, as well as the in-situ fluid properties such as, but not limited to, fluid type and viscosity.

For example, an NMR operation may include applying a static magnetic field to the zone of interest of a substance, e.g., the formation. The static magnetic field may generate an initial magnetization of atomic nuclei within the substance. Then, an NMR system may be used to apply an oscillating magnetic field at a particular frequency to the substance. The oscillating field may be composed of a sequence of pulses (e.g., radio frequency pulses) that tip the magnetization of the atomic nuclei away from the initial magnetization. The sequence of pulses may be arranged so that pulses and the static field interact with the nuclei to produce a resonant signal composed of "echoes" (e.g., spin echoes) within at least a portion of the substance. These echoes (e.g., their amplitude, duration [time], and/or phase) may be sensed and recorded to form an NMR echo data set.

By way of background, NMR well logging tools, e.g., LWD tool 120 of FIG. 1, may use permanent magnets to create a (e.g., strong) static magnetic (e.g., polarizing) field inside the formation. The hydrogen nuclei of certain fluids (e.g., water and hydrocarbons) are electrically charged spinning protons that create a weak magnetic field similar to tiny bar magnets. When a strong external magnetic field (e.g., from the logging tool) passes through a formation containing these fluids, the spinning protons align themselves like compass needles along the magnetic field. This process, generally referred to as polarization, has an exponential recovery to its equilibrium value with $T_1$ (longitudinal relaxation time), while the external magnetic field (generally referred to as the $B_0$ field) is applied by the NMR (e.g., logging) tool.

Figure 2:
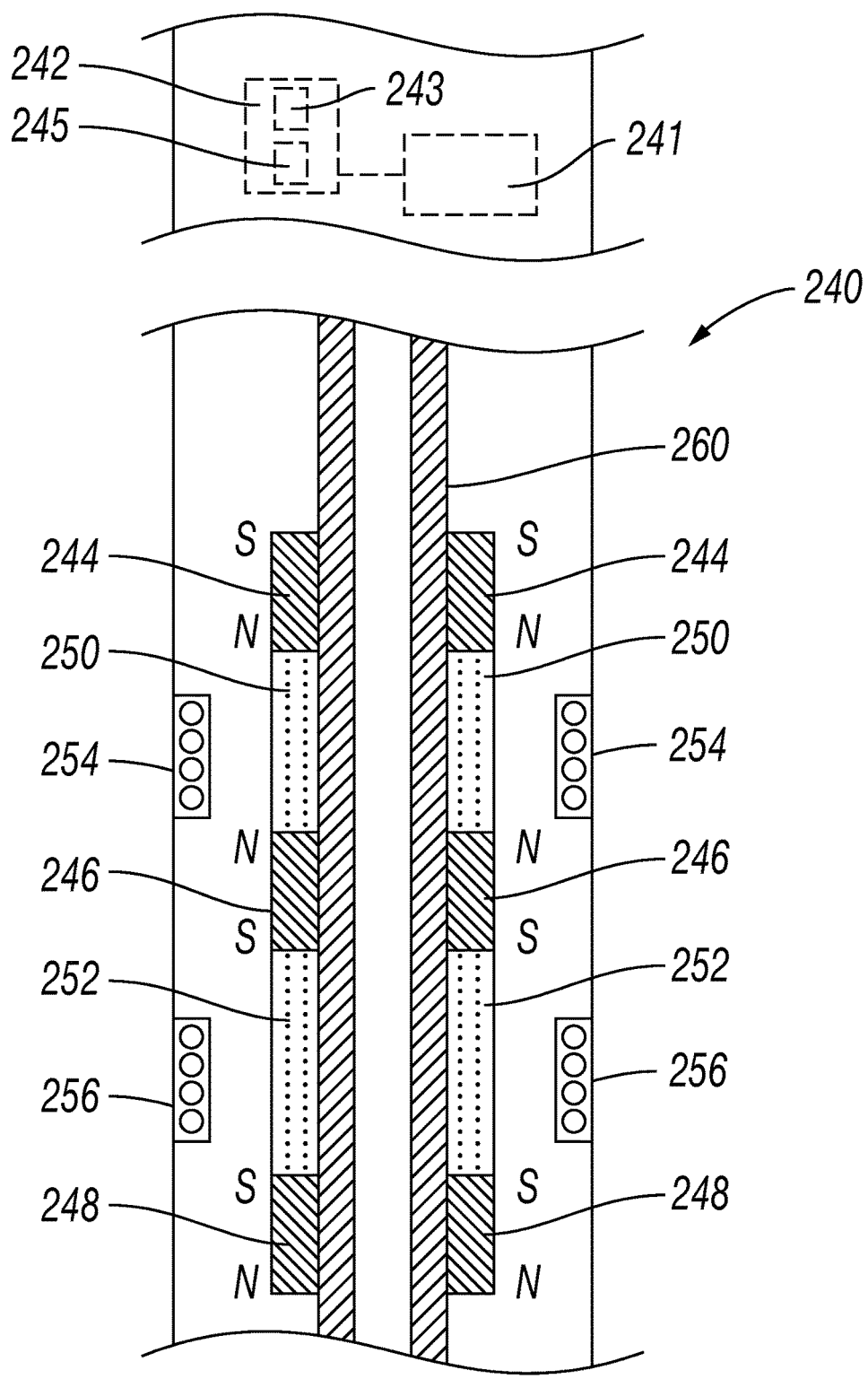
FIG. 2 is an example aspect of a nuclear magnetic resonance (NMR) logging tool that may be used in the well site system of FIG. 1.

FIG. 2 shows an example of an NMR logging tool 240 that is described in commonly assigned U.S. Pat. No. 6,566,874, which is hereby incorporated by reference in its entirety. As an example, the illustrated device in FIG. 2 may be used as the LWD tool 120 or part of an LWD tool suite 120A. Depicted NMR tool 240 includes upper 244, middle 246, and lower 248 permanent magnets that circumscribe an inner protective sleeve 260 of the NMR tool 240. The upper 244 and middle 246 magnets may produce a radial, axisymmetric static $B_0$ field, and the middle 246 and lower 248 magnets may produce another radial, axisymmetric static $B_0$ field. Because, as an example, the upper 244 and middle 246 magnets are closer together than the middle 246 and lower 248 magnets, the upper $B_0$ field may have a higher gradient (and thus, is more sensitive to motion) than the lower $B_0$ field. In some aspects, the north poles of magnets 244 and 246 may face each other to furnish a $B_0$ field that has contour lines that extend radially away from the longitudinal axis of the NMR tool 240; and similarly, the south poles of magnets 246 and 248 may face each other to furnish a $B_0$ field that has contour lines that extend radially into the longitudinal axis of the NMR tool 240. In some aspects, e.g., to produce more uniform $B_0$ fields, the NMR tool 240 may include magnetically permeable sleeves 250 and 252 that circumscribe tie sleeve 260 and may be positioned between the upper 244 and middle 246 magnets and between the middle 246 and lower 248 magnets, respectively.

Among the features of the illustrated NMR tool 240 are that the tool 240 may include a radio frequency (RF) coil 254 which acts as an antenna to transmit signals (e.g., magnetic field pulses, such as $B_1$ pulses) into the formation and to receive spin echo signals for the upper $B_0$ field and/or an RF coil 256 to transmit RF pulses, e.g., $B_1$ pulses, into the formation and to receive spin echo signals. A pulse may be a Gaussian shaped pulse or a square pulse (e.g., in the time domain). The coils 254 and 256 may be coupled to electronic circuitry 242 of the NMR tool 240 that includes, among other things, $B_1$ pulse generators 243 and/or a memory 245 to store NMR data (e.g., echo data that includes indications of the received spin echoes) for example, before transmitting the NMR data uphole. Electronic circuitry 242 may be coupled to a motion device 241 (e.g., an accelerometer, strain gauge, ultrasonic finder and/or a magnetometer) that indicates motion of the NMR tool. This indication may be further processed by the electronic circuitry 242, e.g., before being transmitted uphole in some aspects.

Any NMR tool may be utilized according to various aspects of this disclosure. An NMR tool may include a transmitter to transmit a pulse or sequence of pulses into a zone of interest. An NMR tool may include a receiver to receive an NMR signal (e.g., to cumulatively form an NMR data set). For example, an NMR tool may include a transmitter to transmit an NMR signal (e.g., a pulse or sequence of pulses) and a receiver to receive a different NMR signal. A receiver may have its own antenna or utilize a transmitter's antenna (e.g., when the transmitter is not transmitting).

In operation, NMR data (e.g., echo data) may be acquired by any means known in the art. In one aspect, measurements are obtained by applying a second oscillating magnetic field (generally referred to as the $B_1$ field) as a series of refocusing pulses from an antenna (e.g., coil 54 in FIG. 2) of the NMR tool, which may be followed by or interleaved with data acquisition (e.g., sensing the NMR echo data from the interaction of the magnetic field pulses and the formation). These pulses may be or be based on the Carr-Purcell-Meiboom-Gill (CPMG) pulse sequence or other variants, in which trains of spin echoes are generated by a sequence of refocusing pulses (e.g., a series of pulses and delay time(s) therebetween).

In one aspect, transmitted magnetic field pulses cause the aligned protons to tip into a plane perpendicular (e.g., transverse) to the direction of the magnetization (e.g., polarization) field (e.g., $B_0$). These tipped protons will start to precess, as is known in the art of NMR, around the direction of the (e.g., relatively strong) logging-tool magnetic field ($B_0$) at a frequency called the Larmor frequency. In one aspect, such precessing protons create an oscillating magnetic field which generates relatively weak (e.g., radio frequency) signals at this frequency. The total signal (e.g., amplitude) from the precessing hydrogen nuclei (e.g., a few microvolts) may be a measure of the total hydrogen content, or porosity, of the formation. The NMR data may be the signal that is induced in the zone of interest by the application of a pulse or pulse sequence into the zone of interest. The rate at which the precession decays is generally referred to as the transverse relaxation time ($T_2$), which may be indicative of the rate at which the spinning protons lose their alignment within the transverse plane. The transverse relaxation time ($T_2$) may depend on certain factors, such as: the intrinsic bulk-relaxation rate in the fluid, the surface-relaxation rate, which is an environmental effect, and relaxation from diffusion in a polarized field gradient, which is a combination of environmental and tool effects.

Diffusion coefficients (D) may be measured by the application of a temporary additional gradient in the magnetic field. Diffusion coefficients (D) may be measured in a permanent gradient by applying a sequence of magnetic field pulses with variable non pulse durations (e.g., recovery times where no RF signal is being transmitted into a specific zone of interest) in between, e.g., to encode the diffusive attenuation in spin echo amplitudes. Further, the above NMR echo data and any other NMR data (e.g., of differing measurement types) may be combined to obtain information regarding the formation and/or the fluids present therein. For instance, $T_2$ and D measurements may be combined to obtain two-dimensional information on formation fluids. In another example, $T_2$ and $T_1$ measurements may be combined as well. In general, any NMR measurements including but not limited to the above examples may be combined to obtain multi-dimensional information on the formation or formation fluids.

Once the desired NMR data set is acquired, a mathematical (e.g., inversion) process may be applied to determine the distribution of measured properties that reflects the anisotropy and/or physical, chemical, and molecular properties of formation or formation fluids. For example, the $T_2$ distribution may represent the distribution of pore sizes within the formation, and the area under $T_2$ curve may represent the pore volume filled with formation fluids. Interpretation of pore size distribution and logarithmic mean $T_2$ may be used for calculating various petrophysical parameters, such as permeability and the amount of free and/or bound fluid.

FIG. 3 is a graph of an NMR pulse sequence 300 without a randomizing pulse or sequence of randomizing pulses output into a zone of interest according to one aspect of the disclosure. Particularly, NMR pulse sequence 300 depicted in FIG. 3 is a CPMG pulse sequence having a recovery time ($T_r$) 302 followed by a main refocusing pulse sequence 304 and subsequent multiple burst refocusing pulse sequences 306. Although three burst refocusing pulse sequences (306A, 306B, 306C) are illustrated, a single burst refocusing pulse sequence or a plurality of burst refocusing pulse sequences may be utilized. Furthermore, multiple types of refocusing sequences may be used instead of the main—burst scheme presented in FIG. 3, e.g., with at least one refocusing sequence being repeated. Recovery time 302 is depicted as being after the end of a previous pulse sequence 301. Note that pulse sequence 301 may have been a previous CPMG sequence of pulses. A burst refocusing pulse or pulse sequence may be (e.g., immediately) preceded and/or followed by a recovery time ($T_r$). Each recovery time in a (e.g., CPMG) sequence may be of the same duration (e.g., time $T_{r1}, T_{r2}, \ldots T_{r(final\ sequence)}$) or may be different than other recovery time(s). Depicted recovery times (308A, 308B, 308C) are of the same duration. The vertical lines in FIG. 3 are each schematic representations of a refocusing unit of refocusing pulse(s) surrounded by delay times being applied to a zone of interest, e.g., by an NMR transmitter. In one aspect, each pulse of a pulse sequence is at the same frequency, amplitude, and/or phase angle. For example, a pulse or each pulse may be at a single frequency. In one aspect, a pulse sequence begins with a 90° pulse and is followed by subsequent 180° pulses, which may include delay times therebetween. In one aspect, each pulse of a pulse sequence has the same shape, e.g., a sine function in the time domain of finite duration. In one aspect, the duration (e.g., length) of a main refocusing pulse sequence is at least 2, 3, 4, 5, 6, 7, 8, 9, 10, 100, 1000, etc. times longer than the duration of a burst refocusing pulse sequence in the depicted NMR acquisition scheme. However, the issues of remnant magnetization and the use of randomizing pulse would also apply to any situation where any set of refocusing NMR pulse sequences are repeated, and this is meant to be a non-limiting example.

In one aspect, a CPMG pulse sequence from of an NMR system (e.g., an NMR well logging system) may be utilized to obtain an NMR data set. An accurate model of the main refocusing CPMG pulse sequence and any (e.g., fast and/or shorter duration) burst refocusing CPMG pulse sequences (e.g., repetitions after the main CPMG pulse sequence) may create an NMR data set that is used to accurately obtain multi-dimensional information on the zone of interest and any fluid therein from the NMR acquired data, for example, the formation porosity, fluid type(s), and the formation's pore structure in a downhole logging aspect. A processing assumption (e.g., used in the analysis theories and/or models) may be that the (e.g., CPMG) pulse sequence fully saturates (e.g., zeroes) the magnetization. However, in certain aspects, the NMR data set (e.g., the NMR data set from the zone of interest that is created by the CPMG pulse sequence) such as, but not limited to, the amplitude of the NMR data set, may have inaccuracies (e.g., an offset 310A, 310B, 310C, 310D) due to the build-up of steady state magnetization not accounted for, e.g., in a traditional signal model (for example, the simplified [on resonance saturation] signal model). Although offsets (310A, 310B, 310C, 310D) are depicted as the same value (e.g., height), certain offsets or each offset may differ from other offset(s). In certain aspects, inaccuracies in the NMR data set may lead to (e.g., cause) inaccuracies in the interpretation of the NMR data, e.g., inaccuracies in the porosity of the zone of interest that produced that NMR data set.

In FIG. 3, note that depicted recovery time ($T_r$) is longer than the longitudinal relaxation time ($T_1$). The longitudinal magnetization 312 is indicated by a dashed line in FIG. 3. The longitudinal magnetization (e.g., $M_z$ in a Cartesian coordinate system where the z axis is parallel to the external magnetic field, generally referred to as the static $B_0$ field, applied by the NMR, e.g., logging, tool). In FIG. 3, the longitudinal magnetization is fully recovered (e.g., no net detected residual magnetization of the zone of interest) at the end of $T_r$ and thus is generally equal to the initial magnetization ($M_0$) there. At the end of the depicted main refocusing (e.g., CPMG) pulse sequence 304 in FIG. 3, the echo amplitudes (the peak of each amplitude shown as a circle) have decayed to be generally equal to zero. The end of this depicted main refocusing (e.g., CPMG) pulse sequence is followed by a (e.g., short) recovery time ($T_r$) and then a three (although a single or any plurality of burst or any sort of refocusing pulse sequences may be used) burst refocusing (e.g., CPMG) pulse sequence 306. A first burst refocusing CPMG pulse sequence may be followed by one or more additional burst refocusing CPMG pulse sequences and/or recovery times. For example, $T_r$ may be shorter than $T_1$ and the longitudinal magnetization may partially recover (e.g., not to $M_0$) and the signal amplitude of the NMR data set created from the interaction of the burst refocusing CPMG pulse sequence and the zone of interest may be reduced. This reduction may be used to determine (e.g., infer) $T_1$. This reduction may be used to obtain better statistics for the components with short relaxation times, while the main CPMG with a long $T_r$ (relative to the longest $T_1$) maintains good statistics about the long $T_1$ signals. However, as noted above, inaccuracies (e.g., offsets 310A, 310B, 310C, 310D), for example, due to the build-up of steady state magnetization during a refocusing pulse sequence (e.g. CPMG), may result in the NMR data set from the zone of interest. Inaccuracies may shift the (e.g., echo amplitudes of the) NMR data set such that those inaccuracies cause further inaccuracies in the properties of the zone of interest determined from that data set.

In one example of NMR well wireline logging (WL) and logging while drilling (LWD), an NMR pulse sequence may combine a main refocusing CPMG pulse sequence with a series of burst pulse sequences (e.g., bursts). An example is illustrated in FIG. 3. On resonance, the magnetization at the end of a sufficiently long (e.g., main refocusing) CPMG pulse sequence may be zero and during the recovery time $T_r$, the longitudinal magnetization may recover according to $M_0(1-e^{-T_r/T_1})$. The echo amplitudes from the zone of interest that are induced by the burst refocusing pulse sequences may be used to obtain properties of the zone of interest, such as $T_1$ information and an improved SNR for the short $T_1$ components. This may aid in the determination of basic formation parameters such as porosity, e.g., in formations with fast relaxing components such as shale. There are other ways to obtain this $T_1$ information. For instance, a multiple-frequency pulse may saturate the magnetization followed by a $T_r$ delay and a burst refocusing pulse sequence (e.g., three burst refocusing pulse sequences).

In one aspect of an NMR tool, the NMR data set from the zone of interest may not be accurate when a pulse or the pulses are generally not on resonance for much of the sensitive region of the NMR sensor of a receiver and/or the refocusing pulses are no longer 180° pulses. As shown in FIGS. 4A-7B, burst refocusing pulse sequences in inhomogeneous fields (e.g., in a zone of interest) may have an undesirable offset both theoretically (e.g., in modeling) and with actual measurements (e.g., what the full theory calculations reflect). Certain aspects of this disclosure may be directed to the removal of this residual magnetization, e.g., for accurate analysis of an NMR data set. In prior tools, pulses were added at the end of a main, long CPMG pulse sequence in attempts to reduce the effect of residual magnetization. However, these pulses merely partially suppressed the remnant magnetization (i.e., leaving 2-4 porosity units of magnetization). This disclosure includes aspects where appropriately timed and calibrated (e.g., single frequency) randomizing pulses remove a net detected residual magnetization via their optimization, for example, optimized to an NMR tool.

For 180° refocusing pulse sequences (e.g., pulses) that are on resonance, the echo amplitudes from the zone of interest that are induced by the refocusing pulse sequences may be obtained as follows. During the main refocusing CPMG pulse sequence, the transverse magnetization may decay according to $M_\perp(t)=M_0 e^{-t/T_2}$ (where t refers to the time) and the longitudinal magnetization may go to zero, e.g., $M_z \to 0$. In such an aspect, transverse magnetization may be $M_z$ in a Cartesian coordinate system where the z axis is parallel to the external magnetic field, generally referred to as the static $B_0$ field, applied by the NMR, e.g., logging, tool. $M_\perp$ may also be referred to as $M_{xy}$. After a main refocusing CPMG pulse sequence, the $M_z$ may recover toward $M_0$ with the time constant $T_1$, e.g., $M_z(T_r)=M_0(1-e^{-T_r/T_1})$. Therefore, the initial amplitude of the burst refocusing CPMG pulse sequence may be written as:

$$\frac{M_{\perp,burst}(T_r)}{M_0} = (1 - e^{-T_r/T_1}) \quad (1)$$

The same expression may be utilized for (e.g., each) subsequent burst refocusing pulse sequences (e.g., bursts) and the NMR analyses of the burst refocusing pulse sequence may assume this signal model.

In one example, owing to the spin dynamics in an inhomogeneous magnetic field induced in a zone of interest, the expression of equation (1) may produce inaccuracies, for example, inaccuracies owing to refocusing pulse sequences that are not on resonance (e.g., not 180° pulses).

Certain aspects of this disclosure may be directed to the removal of this residual magnetization, for example, such that the observed burst signal (e.g., NMR data) in an NMR tool may utilize the model of equation (1) without producing inaccuracies in the NMR data set from the zone of interest.

In NMR tools, a magnet may produce an inhomogeneous field and off-resonance effects may be prevalent, e.g., causing inaccuracies in the NMR data set. An off-resonance pulse or pulses may introduce extra terms in the spin dynamics (e.g., in inhomogeneous $B_0$ and/or $B_1$ fields) that result in (e.g., undesirable) longitudinal and/or transverse residual magnetization at the end of a pulse sequence. For example, when $T_1=T_2$ for the zone of interest, the magnetization from a CMPG pulse sequence after the first few (e.g., 2 or 3) echoes may be written in a compact form:

$$\vec{M}_{CPMG}(t)=(\vec{M}(0^+)\cdot\hat{n})\hat{n}e^{-t/T_2}+M_0(\hat{z}\cdot\hat{n})\hat{n}(1-e^{-t/T_{2,eff}}) \quad (2)$$

Note that an arrow above a variable generally refers to the unit vector form. Here $\hat{n}$ is the axis of the composite rotation that describes the evolution from one spin echo to the next and $\vec{M}(0^+)$ is the magnetization after an initial 90° pulse of a CPMG pulse sequence. The first term is generally directly to an on-resonance CPMG pulse sequence's behavior. Close to resonance, $\hat{n}$ may be the transverse plane and $\vec{M}(0^+)$ points along it. The term $(\vec{M}(0^+)\cdot\hat{n})\hat{n}$ may be the transverse magnetization $M_\perp$ that decays with the time constant $T_2$. Off-resonance, $\hat{n}$ may have a longitudinal component, but the associated longitudinal magnetization may also be affected by relaxation and decay to zero at the end of a (e.g., sufficiently long) CPMG pulse sequence.

The second term in equation (2) may grow from zero and become a constant after (e.g., sufficiently long) time. This second term may give rise to the observed inaccuracy (e.g., offset) in the following burst amplitude as standard phase cycling may eliminate its direct observation. The second term may originate from $T_1$ recovery during each echo interval $t_E$. The contribution of $T_1$ recovery during a single echo spacing may scale in proportion to $(t_E/T_1)*M_0$. The part of this magnetization that lies along $\hat{n}$ may be getting refocused and give rise to a (e.g., relatively small) signal $$M_0 \frac{t_E}{T_1}(\hat{z}\cdot\hat{n})\hat{n}e^{-t/T_2}.$$

In some aspects, this incremental signal buildup may be less than 1% of $M_0$, and thus be ignored from (e.g., not included in) the calculation. However, such a signal may originate from each echo interval and these signals may be added coherently (e.g. in phase). The second term of equation (2) generally refers to the sum of these signals. Since it is influences by both $T_2$ and $T_1$, we label it here as an effective $T_2$:$T_{2,eff}$. At certain (e.g., relatively long) times, this second term may become time independent. At the time independent stage, the generation of new magnetization by $T_1$ may be (e.g., fully) canceled by $T_2$ decay such that:

$$\vec{M}_{CPMG}(t\to\infty)=M_0(\hat{z}\cdot\hat{n})\hat{n} \quad (3)$$

This expression may be used for $T_1=T_2$. When $T_1>T_2$, this steady state magnetization may be reduced.

In some applications of a CPMG pulse sequence in inhomogeneous fields, the second term in equation (2) may be ignored from (e.g., not included in) the calculation. In one aspect, the second term in equation (2) may be ignored from (e.g., not included in) the calculation where an implementation of a CPMG pulse sequence includes phase cycling of the initial 90° pulse relative to the 180° pulses, e.g., to eliminate contributions to the signal from the second term completely. In one aspect, even without phase cycling, the second term in equation (2) may be ignored from (e.g., not included in) the calculation when the second term does not generate a detectable signal in the echo window. For example, where the transverse magnetization of this second term generates an echo that coincides with the refocusing pulses when a signal is not acquired.

According to one aspect, a residual magnetization of the zone of interest may affect the signal of a subsequent burst refocusing pulse. For example, at the end of a main refocusing CPMG pulse sequence, pulsing may be stopped and the longitudinal magnetization recovers towards $M_0$ during the recovery time $T_r$:

$$M_z(T_w) = M_0 + [M_z(T_r=0) - M_0]e^{-T_r/T_1} \quad (4)$$

According to one aspect, if the initial main refocusing CPMG pulse sequence has been applied long enough (e.g., for a duration $t_{decayed}$) so that the first term in equation (2) has completely decayed (e.g., to about zero), the longitudinal magnetization $M_z(T_r=0)$ may be given by equation (3) and the longitudinal magnetization just before the first burst refocusing pulse sequence (e.g., burst 306A) may be given by:

$$\frac{M_z(T_r)}{M_0} = (1 - e^{-T_r/T_1}) + (\hat{n}\cdot\hat{z})^2 e^{-T_r/T_1} \quad (5)$$

where the first term corresponds to the on resonance behavior of equation (1). As the second term in equation (5) is positive, the longitudinal magnetization before the first burst may be higher than expected from the on resonance saturation behavior. In one aspect, where $T_r$ is longer than an (e.g., plurality of) echo spacing $t_E$, the transverse magnetization may be dephased and thus be ignored. In that aspect, the magnetization after an initial 90° burst of the burst sequence may be calculated by evaluating the rotation of the initial pulse on the longitudinal magnetization of equation (5): $\mathcal{R}_{90}\{M_z(T_w)\}$. $\mathcal{R}_x$ generally refers to the rotation operator (e.g., rotation operator matrix) as is known in the field of NMR where the subscript x may refer to the axis of the rotation of the pulse relative to the static magnetic field. This $\mathcal{R}_{90}\{M_z(T_w)\}$ term for the first burst refocusing pulse sequence may be considered analogous to $\hat{M}(0^+)$ in equation (2) for the main refocusing pulse sequence. The magnetization for the burst refocusing pulse sequence may then be similar to equation (2) and given by:

$$\hat{M}_{burst1}(t) = (\mathcal{R}_{90}\{M_z(T_r)\}\cdot\hat{n})\hat{n}e^{-t/T_2} + M_0(\hat{z}\cdot\hat{n})\hat{n}(1-e^{-t/T_1}) \quad (6)$$

As discussed above, in this aspect the first term may mainly contribute to the detected signal. By combining equations (5) and (6), the amplitude for the detected signal from zone of interest as induced by the first burst in a burst refocusing CPMG pulse sequence may be proportional to $(1-e^{-T_w/T_1}) + Be^{-T_r/T_1}$ where B is a positive number $0 \le B \le 1$. The magnetic field offset B may be given by:

$$B = \frac{\langle(\hat{z}\cdot\hat{n})^2(\hat{n}\cdot\hat{y})(\mathcal{R}_{90}\{M_z(T_r)\}\cdot\hat{n})\rangle}{\langle(\hat{n}\cdot\hat{y})(\mathcal{R}_{90}\{M_z(T_r)\}\cdot\hat{n})\rangle} \quad (7)$$

Such an analysis may be extended to calculate the signal (e.g., the NMR data set) for each of subsequent bursts. In one aspect, the duration of each burst refocusing CPMG pulse sequence is shorter than the $T_1$ of the zone of interest. In that case, the magnetization at the end of the first burst refocusing CPMG pulse sequence (e.g., 306A) may be dominated by the first term in equation (6). Equation (4) may then be used to calculate the longitudinal magnetization before the second burst refocusing CPMG pulse sequence (e.g., 306B) and reapply equation (6) to calculate the signal of the first burst refocusing CPMG pulse sequence. This procedure may be repeated to calculate further bursts as desired.

In certain NMR tool aspects, the equations for the magnetization and burst signal presented so far may correspond to a specific (e.g., RF) pulse strength and frequency and magnetic field strength. In an aspect where these factors are constant, the CPMG pulse sequence may be calibrated to meet the on resonance condition. However, in certain aspects, these factors may not be constant, e.g., the magnetic field strength and/or the RF pulse strength, may be non-uniform over a tool's sensitive region. The burst signal (e.g., the NMR data set) may then be the sum of the contributions from the different combinations of pulse strengths ($\omega_1$) and resonance frequencies ($\omega_0$) which determine the values for $\hat{n}$ and $\hat{M}(0^+)$ given the specific pulse sequence parameters such as the specific refocusing pulse(s) used and the repetition (e.g. echo) time for the refocusing.

One model for a gradient style NMR tool is to assume a uniform pulse strength ($\omega_1$) and a constant gradient in the magnetic field ($\omega_0$). Turning to FIGS. 4A-7B, they plot the magnetization (e.g., polarization) immediately before a burst refocusing pulse sequence (e.g., 306B) and the burst signal as a function of $\omega_0/\omega_1$. Assuming a uniform magnetic field gradient, the observed signal (e.g., NMR data set) is simply the sum across the $\omega_0/\omega_1$ axis. Note that this model may be generalized to any NMR tool type. For example, this sum may be weighted to match the (e.g., exact) $\omega_0/\omega_1$ distribution of a specific tool or used to analyze another general tool model such as for a saddle point tool.

Particularly, FIGS. 4A-7B illustrate the spectra of the transverse magnetization of a burst pulse sequence for different recovery times $T_r$ as indicated following a main CPMG that reached the steady state signal. For each of FIGS. 4A-7B (such as 4A and 4B), the "A" graph illustrates the simplified (on-resonance) theory spectra for a burst's longitudinal magnetization and the "B" graph illustrates the full theory spectra incorporating remnant magnetization effects that includes the residual magnetization after a pulse sequence causing such residual magnetization. The units of the example offset frequency are $\omega_1 = 2\pi \times 3.84$ kHz.

FIG. 4A is a graph of the simplified (on resonance saturation) theory spectra of the transverse magnetization of a zone of interest from a pulse sequence at a first duration of recovery time ($T_r$) according to one aspect of the disclosure. FIG. 4B is a graph of the full theory spectra of the transverse magnetization of a zone of interest from a pulse sequence at a first duration of recovery time ($T_r$) according to one aspect of the disclosure. FIG. 5A is a graph of the simplified (on resonance saturation) theory spectra of the transverse magnetization of a zone of interest from a pulse sequence at a second duration of recovery time ($T_r$) according to one aspect of the disclosure. FIG. 5B is a graph of the full theory spectra of the transverse magnetization of a zone of interest from a pulse sequence at a second duration of recovery time ($T_r$) according to one aspect of the disclosure. FIG. 6A is a graph of the simplified (on resonance saturation) theory spectra of the transverse magnetization of a zone of interest from a pulse sequence at a third duration of recovery time ($T_r$) according to one aspect of the disclosure. FIG. 6B is a graph of the full theory spectra of the transverse magnetization of a zone of interest from a pulse sequence at a third duration of recovery time ($T_r$) according to one aspect of the disclosure. FIG. 7A is a graph of the simplified (on resonance saturation) theory spectra of the transverse magnetization of a zone of interest from a pulse sequence at a fourth duration of recovery time ($T_r$) according to one aspect of the disclosure. FIG. 7B is a graph of the full theory spectra of the transverse magnetization of a zone of interest from a pulse sequence at a fourth duration of recovery time ($T_r$) according to one aspect of the disclosure.

In the aspects of FIGS. 4A-7B, the on resonance saturation theory of the magnetization at the end of the CPMG (e.g., magnetic polarization is zero at $T_r=0$) often used for the NMR signal analysis breaks down as the signal goes away from resonance. For example, the error for the on resonance saturation model for the burst signal decreases as $T_r/T_1$ decreases in FIGS. 4A-7B, for example, since much of the loss of magnetization (e.g., polarization) that the model falsely predicts by ignoring magnetic field offset B has a chance to recover at longer $T_r$. However, in one aspect the burst refocusing pulse sequence(s) use smaller (e.g., relative to the longest $T_r$ for the full polarization of all detected components) values of $T_r$ to improve sensitivity to smaller $T_1$ components and characterize the distribution of $T_1$ values. Thus, in one aspect burst refocusing pulse sequences may operate (e.g., be generated at) at small values of $T_r/T_1$ for at least some of the possible signals. FIGS. 4A-7B further illustrate that the simplified (on resonance saturation) theory does not account for the (e.g., full) residual magnetization in these aspects. For example, the magnetization detected by the first burst in FIG. 6A is less than the magnetization in FIG. 6B due to the presence of residual magnetization accounted for in FIG. 6B. For a further example, the magnetization detected by the first burst in FIG. 7A is less than the magnetization in FIG. 7B due to the presence of residual magnetization accounted for in FIG. 7B.

Figure 8A:
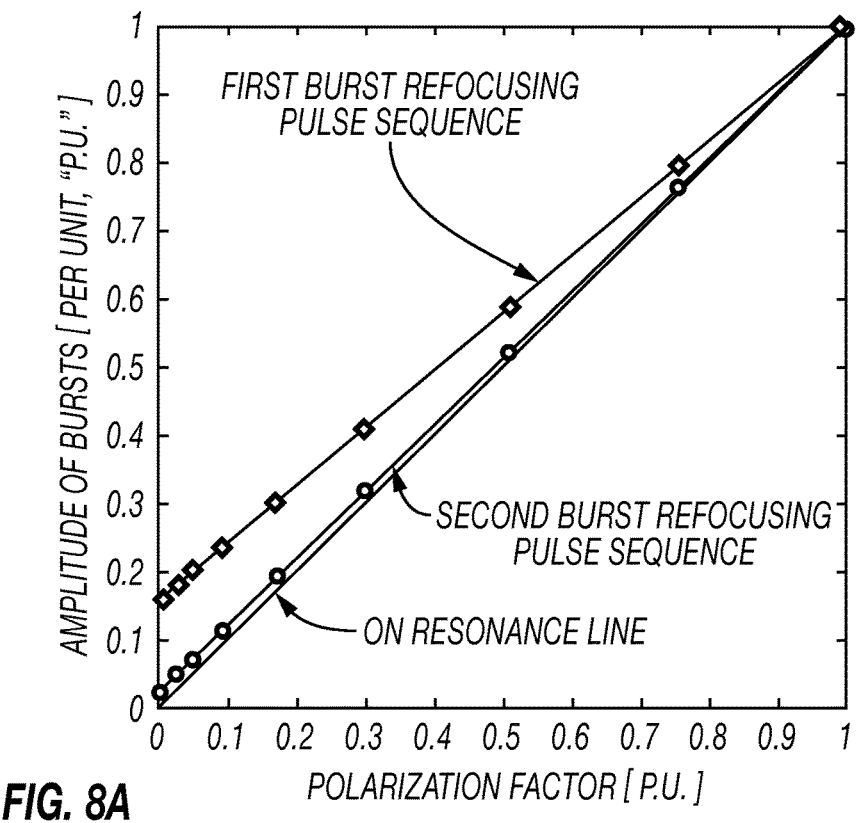
FIG. 8A is a graph of calculated amplitudes of a first and a second burst refocusing pulse sequence for different durations of recovery times ($T_r$) according to one aspect of the disclosure.
Figure 8B:
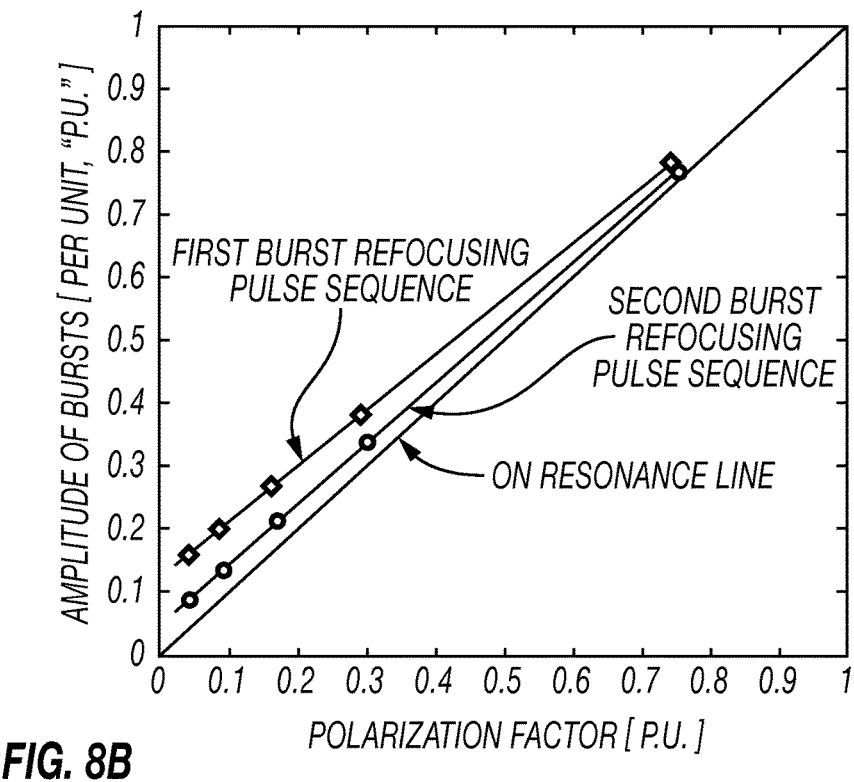
FIG. 8B is a graph of measured amplitudes of a first and a second burst refocusing pulse sequence for different durations of recovery times ($T_r$) according to one aspect of the disclosure.

Turning now to FIGS. 8A-8B, the burst signal (e.g., amplitude of burst refocusing pulse sequences) for a magnetic field gradient type of NMR tool taking residual magnetization into account is plotted versus the polarization factor (e.g., $1-e^{-T_w/T_1}$) for a first burst refocusing pulse sequence, a second burst refocusing pulse sequence, and the ideal on resonance magnetization model (e.g., the on resonance saturation line). FIG. 8A is a graph of calculated amplitudes of a first and a second burst refocusing pulse sequence for different durations of recovery times ($T_r$) according to one aspect of the disclosure. The amplitudes of the NMR data for the first and the second burst refocusing pulse sequence are not on (e.g., they are above) the on resonance saturation line and thus deviate from the on-resonance model for the magnetization left by the prior CPMG (e.g. $M_z(T_r=0)=0$). The illustrated offset at (e.g., short) recovery times is B=0.16. FIG. 8B is a graph of measured amplitudes of a first and a second burst refocusing pulse sequence for different durations of recovery times ($T_r$) according to one aspect of the disclosure. As shown in the model from FIG. 8A, the measured (e.g., from an LWD logging tool) amplitudes of the NMR data for the first and the second burst refocusing pulse sequence are not on (e.g., they are above) the on resonance saturation line and thus not on resonance.

Figure 9:
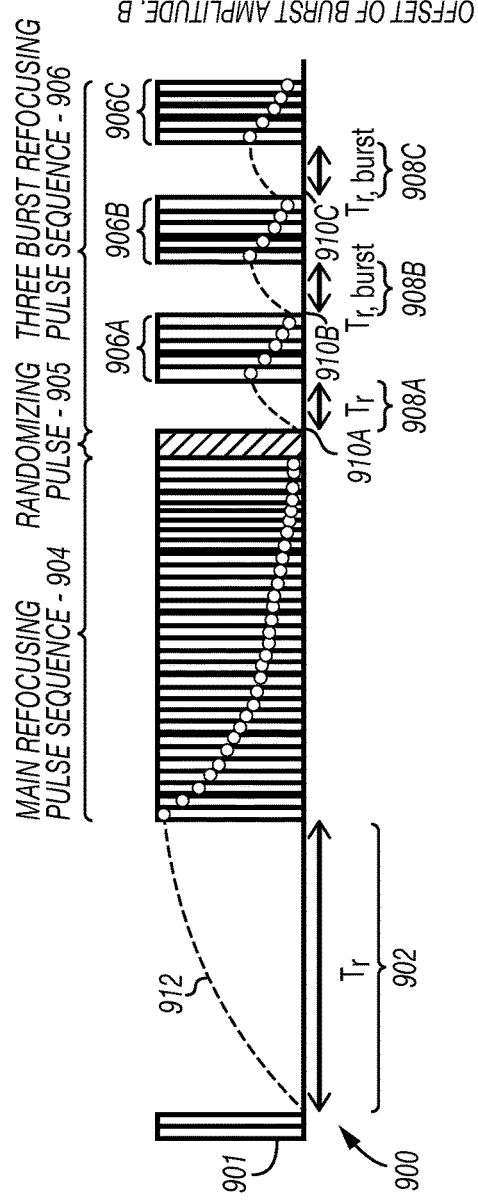
FIG. 9 is a graph of an NMR pulse sequence including a randomizing pulse according to one aspect of the disclosure.

FIG. 9 is a graph of an NMR pulse sequence including a randomizing pulse according to one aspect of the disclosure. A randomizing pulse (e.g., a transmitted signal) or sequence of pulses may be any (e.g., RF) pulse or sequence of pulses to remove a net detected residual magnetization (e.g., effectively scramble any residual magnetization) so the magnetization (e.g., magnetic polarization excited by the next refocusing sequence) sums to zero, for example, to effectively remove any offset and allow for accurate NMR data analysis. This disclosure describes below a single randomizing pulse and a 4 pulse randomizing pulse technique, but any single or plurality of pulses may be utilized. A randomizing pulse or pulses may be used to remove the offset for more accurate data interpretation and may be used with any inhomogeneous NMR device, such as a wireline tool, an LWD tool, an NMR core analyzer, or a portable NMR sensor. A randomizing pulse may be outputted after a delay time or (e.g., immediately) after or (e.g., immediately) before a previous pulse or pulse sequence.

A randomizing pulse may be outputted (e.g., immediately) before or (e.g., immediately) after a main refocusing pulse sequence. A randomizing pulse may be outputted (e.g., immediately) before or (e.g., immediately) after a main refocusing pulse sequence but not after a burst refocusing pulse sequence. A randomizing pulse may be outputted (e.g., immediately) before and (e.g., immediately) after a main refocusing pulse sequence. A randomizing pulse may be outputted (e.g., immediately) before or (e.g., immediately) after a burst refocusing pulse sequence. A randomizing pulse may be outputted (e.g., immediately) before and (e.g., immediately) after a burst refocusing pulse sequence. A randomizing pulse may be outputted (e.g., immediately) before or (e.g., immediately) after each burst refocusing pulse sequence. A randomizing pulse may be outputted (e.g., immediately) before or (e.g., immediately) after a burst refocusing pulse sequence but not (e.g., immediately) after a main refocusing pulse sequence. A recovery (e.g., recovery) time may be included before or after any pulse utilized. Multiple refocusing pulse sequences may each include at least one randomizing pulse or a plurality of randomizing pulses (e.g., a sequence of randomizing pulses).

FIG. 9 is a graph of an NMR pulse sequence 900 utilizing a randomizing pulse 905 output into a zone of interest (e.g., a formation) according to one aspect of the disclosure. Particularly, NMR pulse sequence 900 depicted in FIG. 9 is a CPMG pulse sequence having a recovery time ($T_r$) 902 followed by a main refocusing pulse sequence 904 and multiple burst refocusing pulse sequences 906. Although three burst refocusing pulse sequences (906A, 906B, 906C) are illustrated, a single burst or burst refocusing pulse sequence may be utilized. Recovery time 902 is depicted as being after the end of a previous pulse sequence 901. Note that pulse sequence 901 may have been a previous CPMG sequence of pulses. Pulse sequence 901 may be followed (e.g., immediately) by a randomizing pulse. A burst refocusing pulse or pulse sequence may be (e.g., immediately) preceded and/or followed by a recovery time ($T_r$). Each recovery time in a (e.g., CPMG) sequence may be of the same duration (e.g., time $T_{r1}, T_{r2}, \ldots T_{r(final\ sequence)}$) or may be different than other recovery time(s). Depicted recovery times (908A, 908B, 908C) are of the same duration. The vertical rectangles in FIG. 9 are each schematic representations of refocusing periods for a CPMG which may be a single pulse followed by a delay during which data may be acquired from a zone of interest, e.g., by an NMR receiver. In one aspect, each pulse of a pulse sequence is at the same frequency, amplitude, and/or phase angle. In one aspect, a pulse sequence begins with a 90° pulse and is followed by subsequent 180° pulses, which may include delay times therebetween. In one aspect, each pulse of a pulse sequence has the same shape, e.g., a sine function in the time domain of finite duration. In one aspect, the duration (e.g., length) of a main refocusing pulse sequence is at least 2, 3, 4, 5, 6, 7, 8, 9, 10, 100, 1000, etc. times longer than the duration of a burst refocusing pulse sequence.

In one aspect, a CPMG pulse sequence from of an NMR system (e.g., an NMR well logging system) may be utilized to obtain an NMR data set. An accurate model of the main refocusing CPMG pulse sequence and any (e.g., fast and/or shorter duration) burst refocusing CPMG pulse sequences (e.g., repetitions after the main CPMG pulse sequence) may create an NMR data set that is used to accurately obtain multi-dimensional information on the zone of interest and any fluid therein from the NMR acquired data, for example, the formation porosity, fluid type(s), and the formation's pore structure in a downhole logging aspect. A processing assumption (e.g., used in the analysis theories and/or models) may be that the CPMG pulse sequence fully saturates (e.g., zeroes) the magnetization (e.g., as previously referred to as the on-resonance model in FIGS. 3-7). However, in certain aspects, the NMR data set (e.g., the NMR data set from the zone of interest that is created by the CPMG pulse sequence) such as, but not limited to, the amplitude of the NMR data set, may have (e.g., undesirable) inaccuracies (e.g., an offset such as 310A in FIG. 3) due to the build-up of steady state magnetization not accounted for, e.g., in a traditional signal model (for example, the simplified [on resonance saturation] signal model). In certain aspects, inaccuracies in the NMR data set may lead to inaccuracies in the interpretation of the NMR data, e.g., inaccuracies in the porosity, of the zone of interest that produced that NMR data set.

In FIG. 9, note that depicted recovery time ($T_r$) is longer than the longitudinal relaxation time ($T_1$). The longitudinal magnetization 912 is indicated by a dashed line in FIG. 9. The longitudinal magnetization (e.g., $M_z$ in a Cartesian coordinate system where the z axis is parallel to the external magnetic field, generally referred to as the static $B_0$ field, applied by the NMR, e.g., logging, tool). In FIG. 9, the longitudinal magnetization is fully recovered (e.g., no net detected residual magnetization of the zone of interest) at the end of $T_r$ and thus is generally equal to the initial magnetization ($M_0$) there. At the end of the depicted main refocusing (e.g., CPMG) pulse sequence 904 in FIG. 9, the echo amplitudes (the peak of each amplitude shown as a circle) are forced to be generally equal to zero by randomizing pulse 905. In certain aspects, randomizing pulse 905 may remove a net detected residual magnetization, e.g., such that there is no offset (910B, 910C) in a subsequent burst refocusing pulse sequence or any subsequent burst refocusing pulse sequences. Although not depicted, an additional delay time may be included between the end of a pulse sequence (e.g., 904) and a randomizing pulse (e.g., 905).

In one aspect, a net detected residual magnetization left at the end of a pulse sequence (e.g., CPMG pulse sequence) that includes at least one burst pulse may affect the behavior of the magnetization (e.g., polarization), and thus affect the on resonance saturation model which may be used to determine properties of the zone of interest. For example, any inaccuracies in the magnetization (e.g., polarization) model may carry over into the inverted data used to determine properties of the zone of interest and thus increasing the error.

In one aspect, by using a randomizing pulse outputted into a zone of interest to remove a net detected residual magnetization, the on resonance magnetization (e.g., polarization) model may be utilized instead of a full theory burst magnetization (e.g., polarization) model. In one aspect, an NMR tool may have an (e.g., limited) bandwidth for the (e.g., RF) pulses which may affect both the pulse shape and signal intensity (e.g., amplitude) as a function of $\omega_0$. The (e.g., limited) bandwidth of an NMR tool may alter the residual magnetization detected (e.g., with its receiver) where the residual magnetization primarily arises from off-resonance signals. In one aspect, the (e.g., RF) bandwidth of the NMR tool may vary (e.g., with downhole tool temperature and formation type which may both vary during a single logging run) and the use of a randomizing pulse may allow the NMR tool to be used without calibration for residual magnetization(s) which may be a function of environmental conditions.

According to certain aspects of the disclosure, a randomizing pulse (e.g., as part of a sequence of refocusing pulses) may be utilized such that the NMR data received will follow the on resonance magnetization model. In one aspect, a randomizing pulse (e.g., from a randomizing pulse module of an NMR tool or system) may be used with an NMR tool that utilizes a single (e.g., RF) frequency, for example, a pulse sequence that does not include a multiple frequency pulse and/or does not saturate the magnetization. In one aspect, a randomizing pulse has a constant frequency and a variable time duration.

In one aspect, as a burst signal $$\left(\text{e.g.,} \frac{M_{\perp,burst}(t)}{M_0}\right)$$

sums over a wide range of frequencies, a randomizing pulse may partially (e.g., not fully) saturate the signal. Instead, in such an aspect, the randomizing pulse(s) may scramble the residual magnetization such that the net detected residual magnetization sums to approximately zero when detected by the burst. In certain aspects, a shorter duration (e.g., relative to a CPMG pulse sequence) of a set of pulses or even a single pulse may remove (e.g., suppress) the net detected residual magnetization, and thus have the burst signal obey the on resonance magnetization model, e.g., to produce an NMR data set without any inaccuracies such as offset(s). Three examples of randomizing pulse schemes are discussed below, although any randomizing pulse scheme that removes the net detected residual magnetization may be utilized.

Turning back to FIG. 9, the end of the depicted randomizing pulse 905 is followed by a (e.g., short) recovery time ($T_r$) and then a three (although a single or any plurality of burst pulses may be used) burst refocusing (e.g., CPMG) pulse sequence 906. The first burst refocusing CPMG pulse sequence may be followed by one or more burst refocusing CPMG pulse sequences and/or recovery times. For example, $T_r$ may be shorter than $T_1$ and the longitudinal magnetization may partially recover (e.g., not to $M_0$) and the signal amplitude of the NMR data set created from the interaction of the burst refocusing CPMG pulse sequence and the zone of interest may be reduced. This reduction may be used to determine (e.g., infer) $T_1$. This reduction may be used to obtain better statistics for the components with short relaxation times. However, as noted above, inaccuracies (e.g., offsets), for example, due to the build-up of steady state magnetization, may be removed by a randomizing pulse. Removal of the inaccuracies from a net detected residual magnetization may remove any shift of the (e.g., echo amplitudes of the) NMR data set such that the properties of the zone of interest determined from the data set are accurate.

Figure 10:
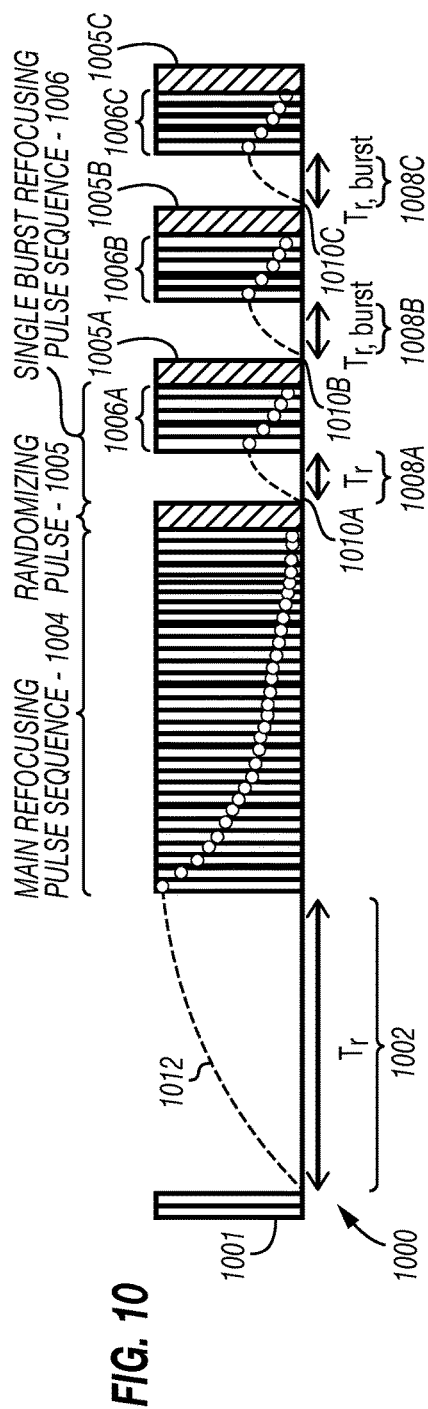
FIG. 10 is a graph of an NMR pulse sequence including randomizing pulses according to one aspect of the disclosure.

FIG. 10 is a graph of an NMR pulse sequence 1000 utilizing a sequence of randomizing pulses (1005, 1005A, 1005B, 1005C) output into a zone of interest (e.g., a formation) according to one aspect of the disclosure. Particularly, NMR pulse sequence 1000 depicted in FIG. 10 is a CPMG pulse sequence having a recovery time ($T_r$) 1002 followed by a main refocusing pulse sequence 1004 and multiple burst refocusing pulse sequences (1006A, 1006B, 1006C), e.g., a first randomizing pulse followed by additional randomizing pulse(s). Depicted burst refocusing pulse sequence 1006 includes burst refocusing pulses 1006A and a recovery time ($T_r$) 1008A. In some aspects, a pulse sequence may include a leading and/or following recovery time after a pulse. In other aspects, a pulse sequence does not include a recovery time or a recovery time that is much less than $T_1$. Although three burst refocusing pulse sequences (1006A, 1006B, 1006C) are illustrated in FIG. 10, a single burst refocusing pulse or a single burst refocusing pulse sequence may be utilized. Furthermore, this may apply to any repetition of refocusing pulse sequences, for example, when using multiple refocusing sequences with diffusion editing (e.g., where the timing of the first one or two echoes is varied for diffusion sensitivity) for improved fluid typing. Recovery time 1002 is depicted as being after the end of a previous pulse sequence 1001. Note that pulse sequence 1001 may have been a previous CPMG sequence of pulses. Pulse sequence 1001 may be followed (e.g., immediately) by a randomizing pulse. A burst refocusing pulse or pulse sequence may be (e.g., immediately) preceded and/or followed by a recovery time ($T_r$). Each recovery time in a (e.g., CPMG) sequence may be of the same duration (e.g., time $T_{r1}, T_{r2}, \ldots T_{r(final\ sequence)}$) or may be different than other recovery time(s). Depicted recovery times (1008A, 1008B, 1008C) are of the same duration. The vertical lines in FIG. 10 are each schematic representations of the refocusing units with each unit having a pulse and a delay, where for CPMG sequences these represent a single pulse delay unit being applied to a zone of interest, e.g., by an NMR transmitter. In one aspect, each pulse of a pulse sequence is at the same frequency, amplitude, and/or phase angle. In one aspect, a pulse sequence begins with a 90° pulse and is followed by subsequent 180° pulses, which may include recovery times therebetween. In one aspect, a pulse sequence begins with an about 90° pulse and is followed by subsequent about 180° pulses, which may include recovery times therebetween. In one aspect, each pulse of a pulse sequence has the same shape, e.g., a sine function in the time domain of finite duration. In one aspect, the duration (e.g., length) of a main refocusing pulse sequence is at least 2, 3, 4, 5, 6, 7, 8, 9, 10, 100, 1000, etc. times longer than the duration of a burst refocusing pulse sequence, for example, the pulse sequences may be the same other than having different durations, e.g., the main sequence being longer than the burst sequence.

The end of the depicted randomizing pulses (1005, 1005A, 1005B, 1005C) in FIG. 10 are each followed by a (e.g., short) recovery time ($T_r$). A first burst refocusing CPMG pulse sequence may be followed by one or more burst refocusing CPMG pulse sequences and/or recovery times interspersed with randomizing pulses. For example, $T_r$ may be shorter than $T_1$ and the longitudinal magnetization may partially recover (e.g., not to $M_0$) and the signal amplitude of the NMR data set created from the interaction of the burst refocusing CPMG pulse sequence and the zone of interest may be reduced. This reduction may be used to determine (e.g., infer) $T_1$. This reduction may be used to obtain better statistics for the components with short relaxation times. However, as noted above, inaccuracies (e.g., offsets), for example, due to the build-up of steady state magnetization, may be removed by a randomizing pulse (e.g., pulse 1205 in FIG. 12C) or randomizing pulses (e.g., pulse sequence 1404 in FIG. 14C). Removal of the inaccuracies from a net detected residual magnetization may remove any shift of the (e.g., echo amplitudes of the) NMR data set such that the properties of the zone of interest determined from the data set are accurate. Each pulse sequence of a multiple pulse sequence (e.g., 1004, 1006A, 1006B, 1006C) may be followed (e.g., immediately or after a recovery time and before a following pulse sequence) by a respective randomizing pulse. A randomizing pulse may be a series of pulses, e.g., output between refocusing pulse sequences.

In some aspects, independent of the implementation of the randomizing pulse (e.g., one randomizing pulse or a sequence of randomizing pulses), a randomizing pulse may be placed (e.g., outputted) anywhere within a series of NMR refocusing pulse sequences (e.g., within a series of CPMG sequence having a main refocusing CPMG pulse sequence followed by at least one burst refocusing CPMG pulse sequence).

One example of a placement scheme is a single randomizing pulse (e.g., one randomizing pulse or a sequence of randomizing pulses) output after a main (e.g., longer than a subsequent burst or any subsequent bursts) refocusing pulse sequence and not after any subsequent burst refocusing pulse sequences, e.g., as in FIG. 9.

Another example of a placement scheme is a plurality of randomizing pulses (e.g., where each of the randomizing pulses includes one randomizing pulse or a sequence of randomizing pulses) output after each of a main (e.g., longer than a subsequent burst) refocusing pulse sequence and any subsequent burst refocusing pulse sequences, e.g., as in FIG. 10.

Yet another example of a placement scheme is a plurality of randomizing pulses (e.g., where each of the randomizing pulses includes one randomizing pulse or a sequence of randomizing pulses) output after each of a main (e.g., longer than a subsequent burst) refocusing pulse sequence and after a subset of subsequent burst refocusing pulse sequences, e.g., after every other burst refocusing sequence or after every two, three, four, etc., burst refocusing pulse sequences. Each randomizing pulse or randomizing pulse sequence may be a 90 degree pulse(s), composite pulse(s), pulses with the same or different frequencies, frequency sweeping pulse(s), phase sweeping pulse(s), or any combination thereof.

Yet another example of a placement scheme is a plurality of randomizing pulses (e.g., where each of the randomizing pulses includes one randomizing pulse or a sequence of randomizing pulses) output after each refocusing pulse sequence expected to produce remnant magnetization (e.g. CPMG length on the order of or much greater than any $T_1$ for a signal component of the sample).

In any placement scheme, a main (e.g., longer than a subsequent burst) (e.g. on the order of or greater than the sample $T_1$) refocusing pulse sequence and/or a subsequent burst refocusing pulse sequence(s), may be any another NMR pulse sequence, such as an NMR pulse sequence ending in a (e.g., longer than or on the order of the sample $T_1$) refocusing sequence resulting in the build-up of residual magnetization. For example, the double echo diffusion editing pulse sequence used in $DT_2$ NMR may replace a main refocusing CPMG pulse sequence and/or a burst refocusing CPMG pulse sequence.

In some aspects, independent of the placement (e.g., output) of a randomizing pulse in an NMR refocusing pulse sequence, implementation of the randomizing pulse (e.g., one randomizing pulse or a sequence of randomizing pulses), may be any pulse (e.g., signal) to remove an (e.g., induced as opposed to naturally occurring) net detected residual magnetization from a zone of interest.

Figure 11:
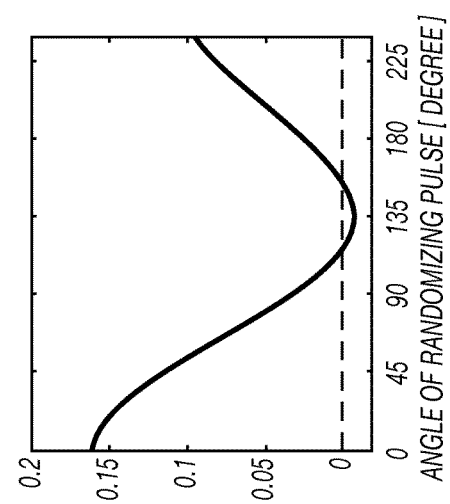
FIG. 11 is a graph of the optimization of a single randomizing pulse in a constant magnetic field gradient NMR tool according to one aspect of the disclosure.

FIG. 11 is a graph of the optimization (e.g., the length and strength) of a single randomizing pulse in a constant magnetic field gradient NMR tool according to one aspect of the disclosure. The single pulse is a one example of a randomizing pulse scheme that may be optimized for an NMR tool to zero the detected net residual magnetization.

FIG. 12A is a graph of the full theory (e.g. incorporates remnant magnetization) spectra of the transverse magnetization of a zone of interest from a pulse sequence without a randomizing pulse according to one aspect of the disclosure. FIG. 12A illustrates the net detected residual magnetization, e.g., induced by a previous pulse sequence without a subsequent randomizing pulse. FIG. 12B is a graph of the full theory spectra of the transverse magnetization of a zone of interest from a pulse sequence including a previous randomizing pulse according to one aspect of the disclosure. FIG. 12B illustrates that the randomizing pulse in this aspect has removed the net detected residual magnetization (e.g., the average of the magnetization data points $M_\perp$ in FIG. 12B is zero). FIG. 12C is a graph of the implementation of a single randomizing pulse 1205 according to one aspect of the disclosure. More particularly, FIG. 12C is a zoomed-in view of a 114 degree randomizing pulse that is output immediately after a main refocusing pulse sequence 1204 and before a burst refocusing pulse sequence 1206, where the randomizing pulse 1205 removes any net detected residual magnetization after that randomizing pulse 1205. For example, having no net detected residual magnetization at point 1210 immediately after the randomizing pulse 1205. Note that in certain aspects, any value of the phase angle of a pulse may be used, with an about 114 degrees pulse being a non-limiting example. Other non-limiting examples are a pulse having a phase angle of about 104 degrees or about 124 degrees. In certain aspects, an NMR randomizing pulse module may optimize a to-be-output randomizing pulse for different tool geometries and/or environments (e.g., tool temperature(s) and/or ambient pressure(s)) for optimal removal (e.g., scrambling) of any net detected residual magnetization. For example, where the distribution of residual magnetization that is initially produced, how it is affected by the randomizing pulse, and finally detected by a following refocusing sequence may depend on the pulse sequence settings (e.g. timing/echo time), RF transmitter characteristics, and magnetic field distribution ($B_1$ and $B_0$). Note that in certain aspects, a randomizing pulse may be in phase with a pulse of a previous pulse sequence.

Figure 13:
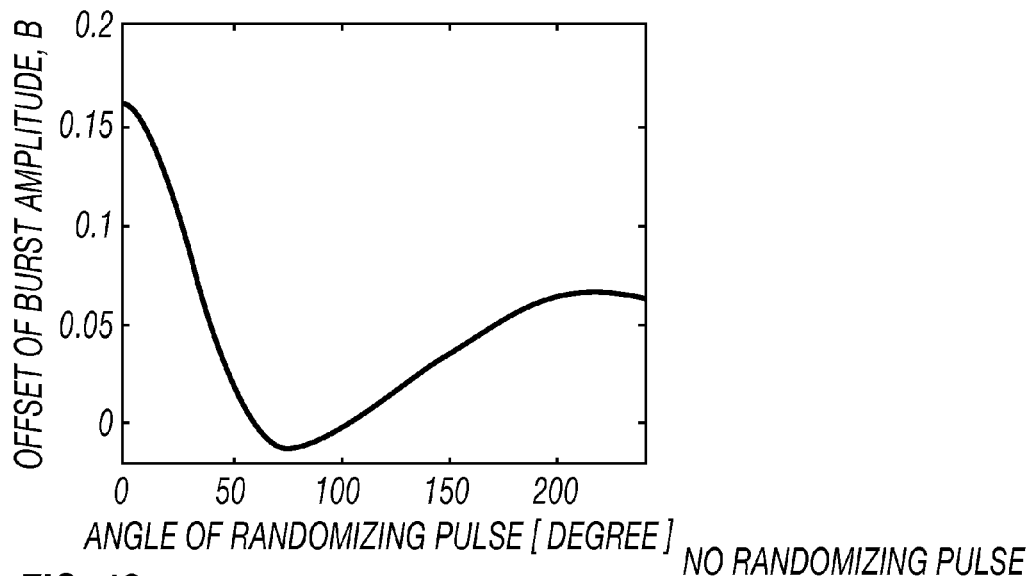
FIG. 13 is a graph of the optimization of each pulse of a multiple pulse randomizing pulse sequence in a constant magnetic field gradient NMR tool according to one aspect of the disclosure.

FIG. 13 is a graph of the optimization of (e.g., the length and strength of) each of a multiple (e.g., 4) pulse randomizing pulse sequence in a constant magnetic field gradient NMR tool according to one aspect of the disclosure. A randomizing pulse sequence may be optimized for variations in the tool and environmental conditions. For example, a multiple-pulse scheme using different pulse axes (e.g., different pulse phases) may randomize the magnetization that coincides with the axis of rotation of the pulse to remove any net detected residual magnetization. Multiple pulse scheme may be utilized to make the sequence insensitive to variations in pulse strength due to changing tool conditions (e.g. temperature, transmitter Q, etc.). By using another pulse, the remaining magnetization along z, may be further reduced whereas the phase may be changed to prevent it from reversing the effect of the prior pulse. Both of these schemes may utilize 4 randomizing pulses, e.g., as this may correspond to the minimum number of pulse phases a CPMG capable spectrometer may produce.

Figure 14A:
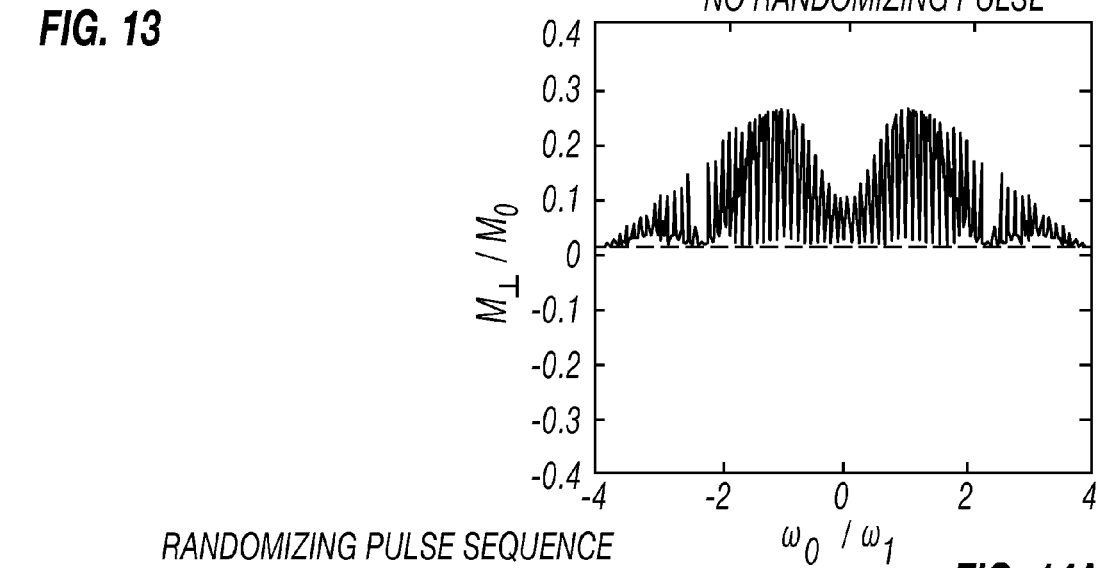
FIG. 14A is a graph of the full theory spectra incorporating remnant magnetization effects of the transverse magnetization of a zone of interest from a pulse sequence without a randomizing pulse according to one aspect of the disclosure.
Figure 14B:
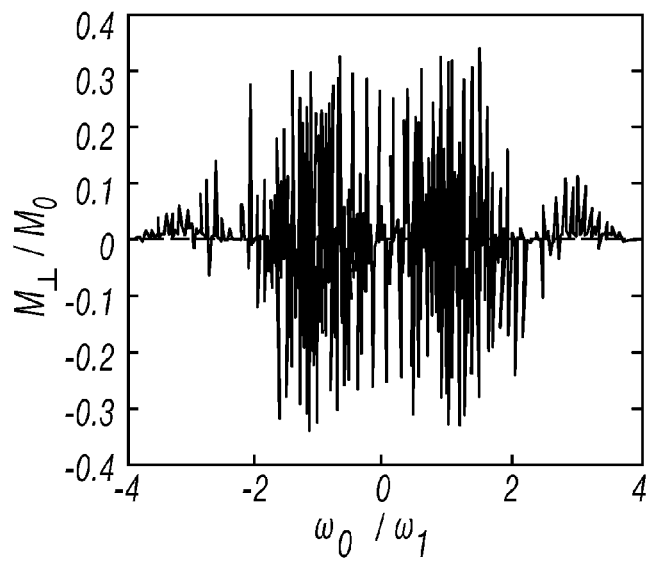
FIG. 14B is a graph of the full theory spectra incorporating remnant magnetization effects of the transverse magnetization of a zone of interest from a pulse sequence including a four pulse randomizing pulse sequence according to one aspect of the disclosure.
Figure 14C:
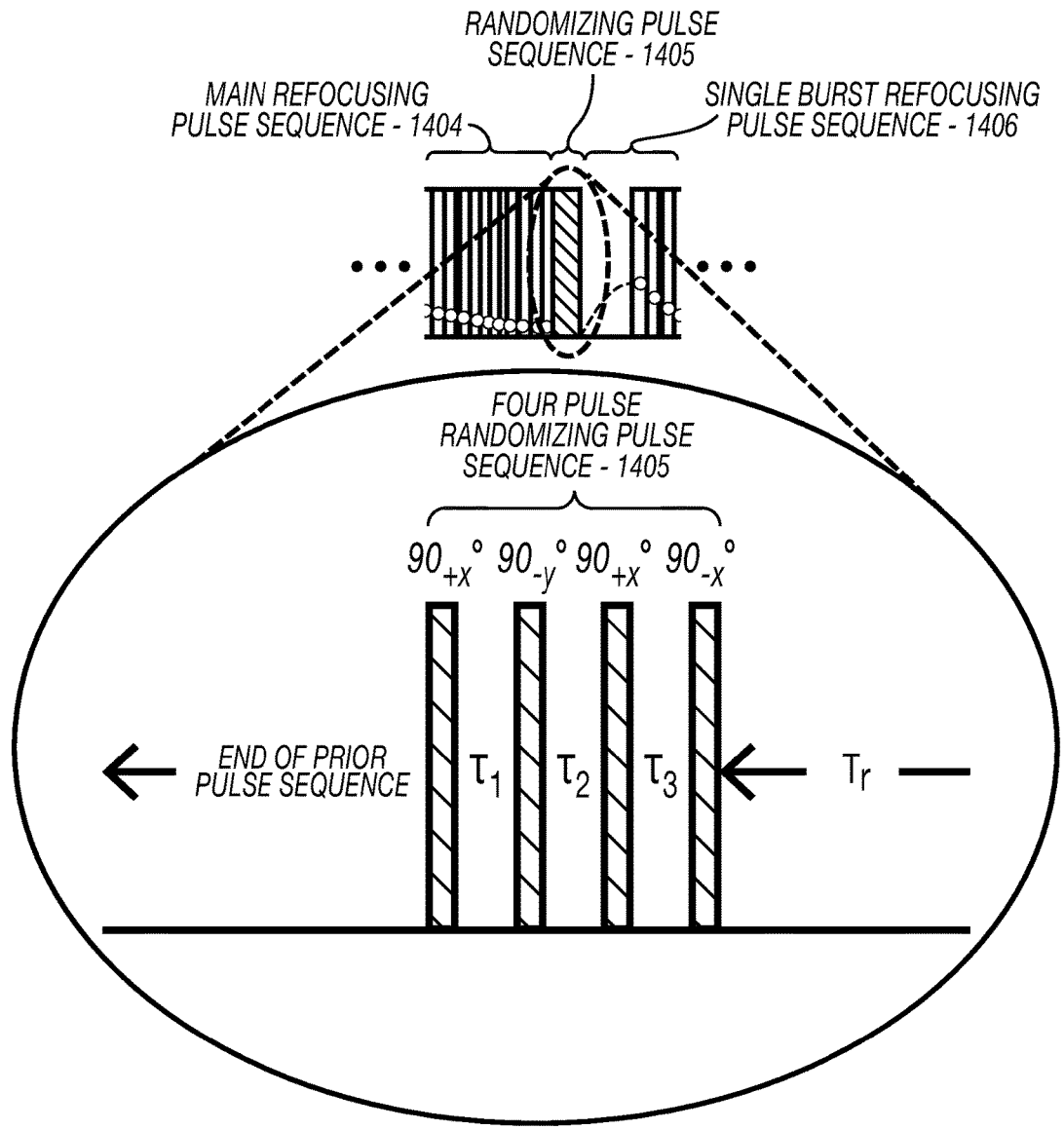
FIG. 14C is a graph of the implementation of a four pulse randomizing pulse sequence according to one aspect of the disclosure.

FIG. 14A is a graph of the full theory (e.g. incorporates remnant magnetization) spectra of the transverse magnetization of a zone of interest from a pulse sequence without a randomizing pulse according to one aspect of the disclosure. FIG. 14A illustrates the net detected residual magnetization, e.g., induced by a previous pulse sequence without a subsequent randomizing pulse or pulses. FIG. 14B is a graph of the full theory spectra of the transverse magnetization of a zone of interest from a pulse sequence including a previous four pulse randomizing pulse sequence according to one aspect of the disclosure. FIG. 14B illustrates that the randomizing pulse sequence in this aspect has removed the net detected residual magnetization (e.g., the average of the magnetization data points $M_\perp$ in FIG. 14B is zero). FIG. 14C is a graph of the implementation of a four pulse randomizing pulse sequence 1405 according to one aspect of the disclosure. More particularly, FIG. 14C is a zoomed-in view of a 4 pulse randomizing pulse sequence that is output immediately after a main refocusing pulse sequence 1404 and before a burst refocusing pulse sequence 1406, where the randomizing pulse sequence 1405 removes any net detected residual magnetization after that randomizing pulse sequence 1405. For example, having no net detected residual magnetization at point 1410 immediately after the randomizing pulse 1405. In one aspect, where the z axis of the Cartesian coordinate system is parallel to the external magnetic field (generally referred to as the static $B_0$ field or the bulk magnetization vector) applied by the NMR (e.g., logging) tool, a randomizing pulse may be applied along one of the Cartesian axes (x, y, −x, −y). A randomizing pulse sequence may include multiple (e.g., two, three, four, five, six, seven, eight, etc.) pulses with phases of about 90 degrees in the +x direction, the −y direction, the +x direction, and the −x direction, e.g., the ($90°_{+x}$, $90°_{-y}$, $90°_{+x}$, $90°_{-x}$) four pulse randomizing pulse sequence in FIG. 14C. Other non-limiting examples of four pulse randomizing pulse sequences include ($90°_{+x}$, $90°_{+y}$, $90°_{-x}$, $90°_{-y}$) and ($90°_{+x}$, $90°_{-y}$, $90°_{+x}$, $90°_{+x}$). Delay times between randomizing pulses may be of the same duration (e.g., time $\tau_1 = \tau_2 = \tau_3$ in FIG. 14C) or may be different than other wait time(s). Note that in certain aspects, any value of the phase angle and/or direction of a pulse may be used, with an about 90 degree pulse being a non-limiting example. In certain aspects, an NMR randomizing pulse module may optimize a to-be-output randomizing pulse and/or pulse sequence for different tool geometries and/or environments (e.g., tool temperatures and/or exposed pressure) for optimal removal (e.g., scrambling) of any net detected residual magnetization. In certain aspects, each pulse of a sequence of two or more (e.g., sequential) randomizing pulses may be at the same frequency.

In another aspect, a burst refocusing pulse sequence may be utilized as a randomizing pulse sequence. For example, any data corresponding to that particular burst refocusing pulse sequence may be removed (e.g., ignored) from the NMR data set while using that burst refocusing pulse sequence as the randomizing pulse sequence that removes the net detected residual magnetization from the zone of interest.

FIG. 15A is graph of an NMR pulse sequence without a randomizing pulse according to one aspect of the disclosure. Depicted NMR pulse sequence includes a main (e.g., refocusing) pulse sequence 1504, then a recovery time ($T_r$) 1508 followed by a burst (e.g., refocusing) pulse sequence 1506. Main (e.g., refocusing) pulse sequence 1504 may induce a net detected residual magnetization 1510 ($M_z$; shown being normalized against $M_0$) in a zone of interest at the end of the main (e.g., refocusing) pulse sequence 1504. The net detected residual magnetization 1510 ($M_z$; shown being normalized against $M_0$) may remain in the zone of interest after a burst (e.g., refocusing) pulse sequence 1506. FIG. 15B is a graph of the full theory spectra of the transverse magnetization of the zone of interest from a burst refocusing pulse sequence of a pulse sequence without a randomizing pulse according to one aspect of the disclosure. Particularly, FIG. 15B depicts the residual magnetization (e.g., 1510) in the zone of interest. FIG. 15C is a graph of the echo signal (e.g., normalized to unit amplitude for full polarization ($M_z=M_0$)) of a burst refocusing pulse sequence of a pulse sequence without a previous randomizing pulse according to one aspect of the disclosure. Particularly, FIG. 15C depicts the net detected residual magnetization in an echo signal of NMR data produced from the zone of interest. The vertical axis represents the normalized, detected echo signal and the horizontal axis represents $t/t_{180}$. As noted above, such residual magnetization may be undesirable in an NMR (e.g., echo) data set.

FIG. 16A is graph of an NMR pulse sequence including a randomizing pulse according to one aspect of the disclosure. Depicted NMR pulse sequence includes a main (e.g., refocusing) pulse sequence 1604, then a randomizing pulse 1605, then a recovery time ($T_r$) 1608 followed by a burst (e.g., refocusing) pulse sequence 1606. Main (e.g., refocusing) pulse sequence 1604 may induce a net detected residual magnetization. Randomizing pulse 1605 output after main (e.g., refocusing) pulse sequence 1604 may remove the net detected residual magnetization 1610 ($M_z$, shown being normalized against $M_0$) in a zone of interest after the end of the main (e.g., refocusing) pulse sequence 1604 that would be detected by the following refocusing sequence 1606. The removal of the net detected residual magnetization 1610 ($M_z$; shown being normalized against $M_0$) (e.g., scrambling of the residual magnetization) in the zone of interest may remain removed after a subsequent burst (e.g., refocusing) pulse sequence 1606. FIG. 15B is a graph of the full theory spectra of the transverse magnetization of the zone of interest from a burst refocusing pulse sequence of a pulse sequence with a randomizing pulse according to one aspect of the disclosure. Particularly, FIG. 16B depicts that there is no net detected residual magnetization (e.g., 1610) in the zone of interest (e.g., the average of the residual magnetization is zero for what would be detected by the following refocusing sequence). FIG. 16C is a graph of the echo signal (e.g., normalized to unit amplitude for full polarization ($M_z=M_0$)) of a burst refocusing pulse sequence of a pulse sequence with a previous randomizing pulse according to one aspect of the disclosure. Particularly, FIG. 16C depicts no net detected residual magnetization (e.g., the average of the residual magnetization is zero) in an echo signal of NMR data produced from the zone of interest. The vertical axis represents the normalized, detected echo signal and the horizontal axis represents $t/t_{180}$. As noted above, no net detected residual magnetization may be desirable in an NMR (e.g., echo) data set.

Figure 17:
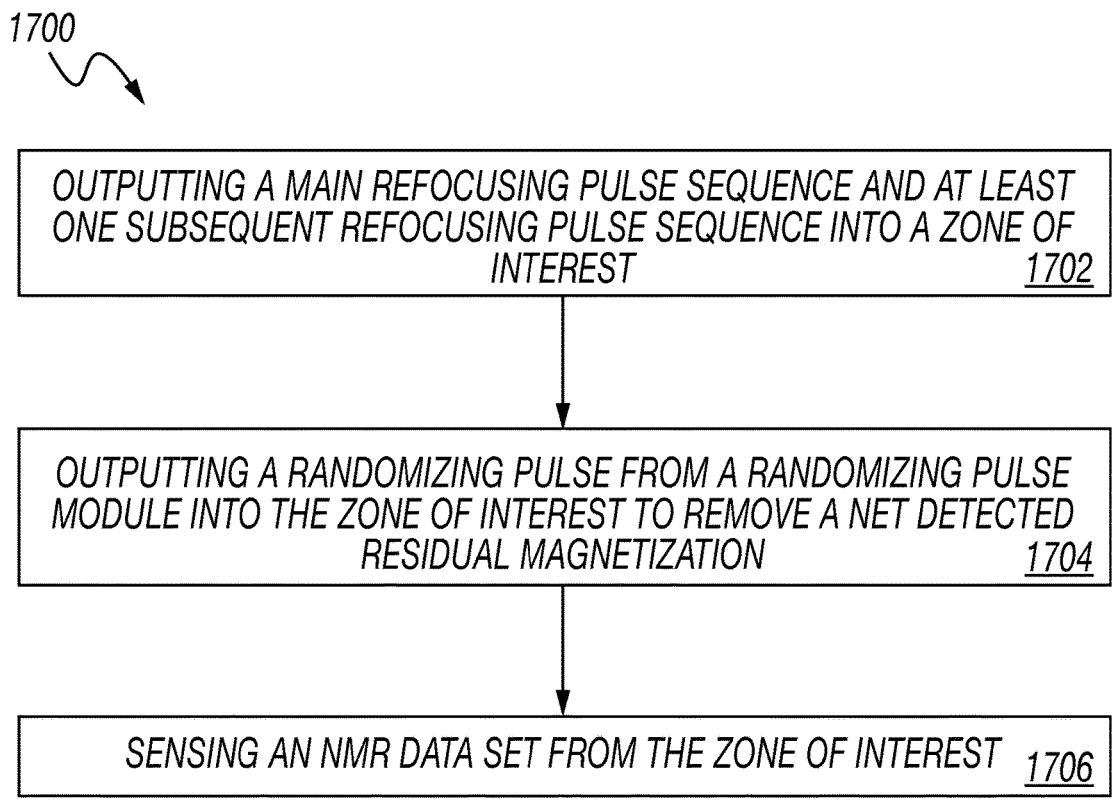
FIG. 17 illustrates an aspect of a method of generating an NMR echo data set.

FIG. 17 illustrates an aspect of a method of generating an NMR echo data set. The depicted method includes outputting a main refocusing pulse sequence and at least one subsequent (e.g., burst or other) refocusing pulse sequence into a zone of interest 1702, outputting a randomizing pulse from a randomizing pulse module into the zone of interest to remove a net detected residual magnetization 1704, and sensing an NMR data set from the zone of interest 1706.

Figure 18:
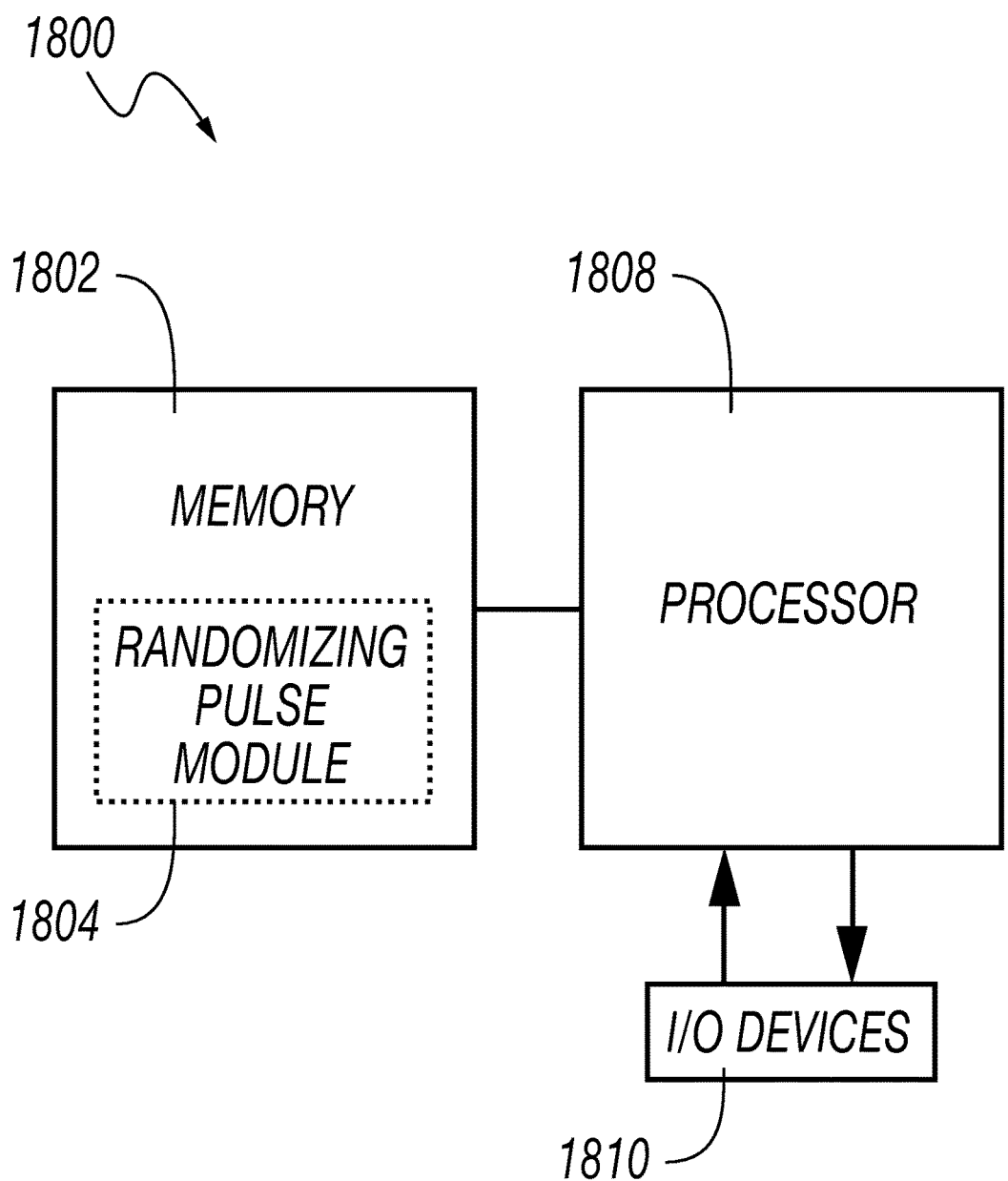
FIG. 18 illustrates an aspect of a block diagram of a computer architecture.

FIG. 18 illustrates an aspect of a block diagram of a computer architecture 1800. Various I/O devices 1810 may be coupled (e.g., via a bus) to processor 1808, for example, a keyboard, mouse, audio device, display device, and/or communication device. Memory 1802 may be coupled to processor 1808. Memory 1802 may include a disk drive or other (e.g., mass) data storage device which may include instructions/code and data, in one aspect. Note that other architectures are possible.

Aspects of the disclosure disclosed herein may be implemented in hardware, software, firmware, or a combination of such implementation approaches. Aspects of the disclosure may be implemented as computer programs or program code executing on programmable systems comprising at least one processor, a storage system (including volatile and nonvolatile memory and/or storage elements), at least one input device, and at least one output device.

Program code may be applied to input instructions to perform the functions and methods described herein and generate output information (e.g., a randomizing pulse and/or NMR echo data that does not include a net detected residual magnetization). The output information may be applied to one or more output devices, in known fashion. For purposes of this application, a processing system includes any system that has a processor, such as, for example, a digital signal processor (DSP), a microcontroller, an application specific integrated circuit (ASIC), or a microprocessor.

The program code may be implemented in a high level procedural or object oriented programming language to communicate with a processing system. The program code may also be implemented in assembly or machine language, if desired. The disclosure herein is not limited in scope to any particular programming language. The language may be a compiled or interpreted language.

One or more aspects may be implemented by representative instructions stored on a machine-readable medium which represents various logic within the processor, which when read by a machine causes the machine to fabricate logic to perform the techniques described herein. Such implementations may be stored on a tangible, non-transitory machine readable medium.

Such machine-readable storage mediums may include, without limitation, non-transitory, tangible arrangements of articles manufactured or formed by a machine or device, including storage media such as hard disks, any other type of disk including floppy disks, optical disks, compact disks (e.g., CD-ROMs or CD-RWs), and magneto-optical disks, semiconductor devices such as read memories (ROMs, random access memories (RAMs) such as dynamic random access memories (DRAMs), static random access memories (SRAMs), erasable programmable read memories (EPROMs), flash memories, electrically erasable programmable read memories (EEPROMs), phase change memory (PCM), magnetic or optical cards, or any other type of media suitable for storing electronic instructions.

Accordingly, aspects of the disclosure also include nontransitory, tangible machine-readable media containing instructions or containing design data, such as Hardware Description Language (HDL), which defines structures, circuits, apparatuses, processors and/or system features described herein. Such aspects may also be referred to as program products. Modules may be implemented in software, hardware, firmware, or a combination thereof. The instruction converter may be on processor, off processor, or part on and part off processor.

In one aspect, memory 1802 is a non-transitory machine readable storage medium having instructions that, when executed, causes a machine to perform a method according to the above disclosure. Particularly, memory 1582 may contain a randomizing pulse module 1804. NMR randomizing pulse module 1584 may include instructions that, when executed, cause the processor to perform a method of generating and/or outputting a randomizing pulse or sequence of randomizing pulses, e.g., according to the disclosure above.

While the specific aspects described above have been shown by way of example, it will be appreciated that many modifications and other aspects will come to the mind of one skilled in the art having the benefit of the teachings presented in the foregoing description and the associated drawings. Accordingly, it is understood that various modifications and aspects are intended to be included within the scope of the appended claims.

What is claimed is:

1. A nuclear magnetic resonance (NMR) system comprising:
   a radio frequency (RF) transmitter to output a main RF refocusing pulse sequence and at least one subsequent RF refocusing pulse sequence into a zone of interest;
   a randomizing pulse module to output an RF randomizing pulse into the zone of interest to remove a net detected residual magnetization caused by the main RF refocusing pulse sequence and/or the at least one subsequent RF refocusing pulse sequence; and
   a receiver to output an NMR data set from the zone of interest.

2. The nuclear magnetic resonance system of claim 1, wherein the RF randomizing pulse is on resonance with at least one of the main RF refocusing pulse sequence and the at least one subsequent RF refocusing pulse sequence to be output immediately prior to the output of the RF randomizing pulse.

3. The nuclear magnetic resonance system of claim 1, wherein the RF randomizing pulse is a single frequency pulse.

4. The nuclear magnetic resonance system of claim 1, wherein the main RF refocusing pulse sequence comprises a Carr-Purcell-Meiboom-Gill (CPMG) pulse sequence and the RF randomizing pulse is on resonance with the CPMG pulse sequence.

5. The nuclear magnetic resonance system of claim 1, wherein the randomizing pulse module is to output the RF randomizing pulse into the zone of interest between the output of the main RF refocusing pulse sequence and the output of the at least one subsequent RF refocusing pulse sequence.

6. The nuclear magnetic resonance system of claim 5, wherein the randomizing pulse module is to output an additional RF randomizing pulse into the zone of interest after the output of each subsequent RF refocusing pulse sequence.

7. The nuclear magnetic resonance system of claim 1,
   wherein at least one of the main RF refocusing pulse sequence and the at least one subsequent RF refocusing pulse sequence is a CPMG pulse sequence, and
   wherein the RF randomizing pulse is an about 114° pulse and in phase with an about 90° pulse of the CPMG pulse sequence to be output immediately prior to the output of the RF randomizing pulse.

8. The nuclear magnetic resonance system of claim 1,
   wherein at least one of the main RF refocusing pulse sequence and the at least one subsequent RF refocusing pulse sequence is a CPMG pulse sequence,
   wherein the RF randomizing pulse is in phase with an about 90° pulse of the CPMG pulse sequence to be output immediately prior to the output of the RF randomizing pulse, and
   wherein a duration of the RF randomizing pulse is adjustable to remove the net detected residual magnetization of the zone of interest.

9. The nuclear magnetic resonance system of claim 1, wherein the randomizing pulse module is to output an RF randomizing pulse sequence into the zone of interest to remove the net detected residual magnetization.

10. The nuclear magnetic resonance system of claim 9, wherein the RF randomizing pulse sequence comprises about 90° pulses.

11. The nuclear magnetic resonance system of claim 1, wherein the receiver is to remove from the NMR data set any NMR data produced in the zone of interest by the RF randomizing pulse.

12. A nuclear magnetic resonance (NMR) method of generating a data set, the method comprising:
   (a) deploying an NMR logging tool in a subterranean wellbore, the NMR logging tool including a radio frequency (RF) transmitter and a receiver;
   (b) causing the RF transmitter to output a main RF refocusing pulse sequence and at least one subsequent RF refocusing pulse sequence into a zone of interest surrounding the wellbore;
   (c) causing the RF transmitter to output an RF randomizing pulse from a randomizing pulse module into the zone of interest to remove a net detected residual magnetization caused by the main RF refocusing pulse sequence and/or the at least one subsequent RF refocusing pulse sequence;
   (d) causing the receiver to sense the NMR data set from the zone of interest; and
   (e) causing a processor to use the NMR data set to determine at least one property of the zone of interest.

13. The NMR method of claim 12, wherein (c) comprises outputting the RF randomizing pulse that is on resonance with at least one of the main RF refocusing pulse sequence and the at least one subsequent RF refocusing pulse sequence that is output in (b) immediately prior to the output of the RF randomizing pulse in (c).

14. The NMR method of claim 12, wherein (c) comprises outputting the RF randomizing pulse that is a single frequency pulse.

15. The NMR method of claim 12, wherein the main RF refocusing pulse sequence comprises a Carr-Purcell-Meiboom-Gill (CPMG) pulse sequence and (c) comprises outputting the RF randomizing pulse that is on resonance with the CPMG pulse sequence.

16. The NMR method of claim 12, wherein the RF randomizing pulse is output in (c) into the zone of interest between the output of the main RF refocusing pulse sequence in (b) and the output of the at least one subsequent RF refocusing pulse sequence in (b).

17. The NMR method of claim 16, wherein (c) further comprises causing the transmitter to output an additional RF randomizing pulse from the randomizing pulse module into the zone of interest after the output of each subsequent RF refocusing pulse sequence in (b).

18. The NMR method of claim 12,
   wherein at least one of the main RF refocusing pulse sequence and the at least one subsequent RF refocusing pulse sequence output in (b) is a CPMG pulse sequence, and
   wherein the RF randomizing pulse output in (c) is an about 114° pulse and in phase with an about 90° pulse of the CPMG pulse sequence, the RF randomizing pulse being output in (c) immediately after the CPMG pulse sequence output in (b).

19. The NMR method of claim 12,
wherein at least one of the main RF refocusing pulse sequence and the at least one subsequent RF refocusing pulse sequence output in (b) is a CPMG pulse sequence,
wherein the RF randomizing pulse output in (c) is in phase with an about 90° pulse of the CPMG pulse sequence, the RF randomizing pulse being output in (c) immediately after the CPMG pulse sequence output of the randomizing pulse in (b), and
further comprising causing a processor to adjust a duration of the RF randomizing pulse to remove the net detected residual magnetization of the zone of interest.

20. The NMR method of claim 12, wherein outputting the RF randomizing pulse in (c) comprises outputting a RF randomizing pulse sequence into the zone of interest to remove the net detected residual magnetization.

21. The NMR method of claim 20, wherein the RF randomizing pulse sequence output in (c) comprises about 90° pulses.

22. The NMR method of claim 12, wherein (e) further comprises causing the processor to removes from the NMR data set sensed in (d) any NMR data produced in the zone of interest by the RF randomizing pulse output in (c).

23. The NMR method of claim 12, wherein (e) further comprises causing the processor to determine the at least one property of the zone of interest with an on resonance magnetization model including the NMR data set sensed in (d).

\* \* \* \* \*